United States Patent [19]

Kato et al.

[11] Patent Number: 4,988,698
[45] Date of Patent: Jan. 29, 1991

[54] 2(1H)-QUINOLINONE COMPOUNDS AND PHARMACEUTICAL COMPOSITION COMPRISING THE SAME

[75] Inventors: Masayuki Kato, Kyoto; Shigetaka Nishino, Osaka; Kiyotaka Ito, Ikeda; Hisashi Takasugi, Osaka, all of Japan

[73] Assignee: Fujisawa Pharmaceutical Co., Ltd., Osaka, Japan

[21] Appl. No.: 434,256

[22] Filed: Nov. 13, 1989

[30] Foreign Application Priority Data

Nov. 21, 1988 [GB] United Kingdom ............... 8827189

[51] Int. Cl.$^5$ .................. A61K 31/495; C07D 521/00
[52] U.S. Cl. .................................... 514/284; 544/284; 544/363
[58] Field of Search ...................... 544/363, 284, 254

[56] References Cited

U.S. PATENT DOCUMENTS 4,886,809 12/1989 Tamada et al. .................... 544/363

Primary Examiner—Richard L. Raymond
Assistant Examiner—James H. Turnipseed
Attorney, Agent, or Firm—Oblon, Spivak, McClelland, Maier & Neustadt

[57] ABSTRACT

This invention relates to new 2(1H)-quinolinone compounds having the formula:

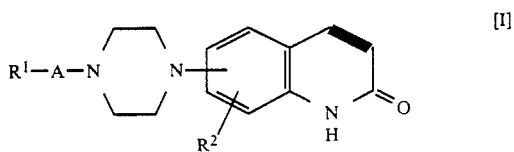

wherein
$R^1$ is a imidazopyridyl, thiazolyl, indolyl, dihydroindolyl, imidazolyl, benzimidazolyl, quinolyl, isoquinolyl, quinazolinyl, dihydroisoquinolyl, tetrahydroimidazopyridyl or tetrahydroquinolyl, each of which may be substituted with substituents(s) selected from the group consisting of lower alkyl, halogen, lower alkoxy, lower alkylthio, ar(lower)alkoxy, cyano, nitro, amino, lower alkylamino, acylamino, hydroxy and oxo,
$R^2$ is hydrogen, lower alkyl or halogen,
A is a single bond or a group of the formula selected from the group consisting of:

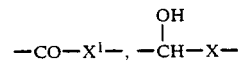

and —X—CO—, in which
X is a single bond or lower alkylene and
$X^1$ is lower alkylene, and
a heavy solid line means a single or a double bond,
and its pharmaceutically acceptable salt. Said compounds are used in the therapeutic treatment of heart diseases and hypertension in human beings and other animals.

6 Claims, No Drawings

2(1H)-QUINOLINONE COMPOUNDS AND PHARMACEUTICAL COMPOSITION COMPRISING THE SAME

This invention relates to new 2(1H)-quinolinone compounds and pharmaceutically acceptable salts thereof.

More particularly, this invention relates to now 2(1H)-quinolinone compounds and pharmaceutically acceptable salts thereof which have pharmacological activities, processes for the preparation thereof, a pharmaceutical composition comprising the same and method for the therapeutic treatment thereby.

One object of this invention is to provide the new and useful 2(1H)-quinolinone compounds and pharmaceutically acceptable salts thereof which possess cardiotonic and hypotensive activities and the capability of reducing heart rate.

Another object of this invention is to provide processes for the preparation of the 2(1H)-quinolinone compounds and salts thereof.

A further object of this invention is to provide a pharmaceutical composition comprising, as active ingredients, said 2(1H)-quinolinone compounds or pharmaceutically acceptable salts thereof.

Still further object of this invention is to provide a method for therapeutic treatment and/or prevention of heart diseases and hypertension of human beings or animals by administering said 2(1H)-quinolinone compounds or pharmaceutically acceptable salts thereof, and more particularly to provide a method for the treatment and/or prevention of cardiac insufficiency, mitral valvular disease, atrial fibrilation, atrial flutter, paroxysmal atrial tachycardia, hypertension and the like. Additionally, the object compound of this invention is expected to be useful as therapeutic and/or preventive agent for peripheral circular diseases, arrhythmia, angina pectoris, myocardiopathy and the like.

The object 2(1H)-quinolinone compounds of this invention are novel and can be represented by the following general formula [I]:

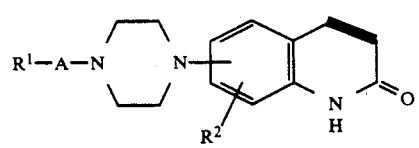

[I]

wherein
$R^1$ is imidazopyridyl, thiazolyl, indolyl, dihydroindolyl, imidazolyl, benzimidazolyl, quinolyl, isoquinolyl, quinazolinyl, dihydroisoquinolyl, tetrahydroimidazopyridyl or tetrahydroquinolyl, each of which may be substituted with substituent(s) selected from the group consisting of lower alkyl, halogen, lower alkoxy, lower alkylthio, ar(lower)alkoxy, cyano, nitro, amino, lower alkylamino, acylamino, hydroxy and oxo,
$R^2$ is hydrogen, lower alkyl or halogen,
A is a single bond or a group of the formula selected from the group consisting of: $-CO-X^1-$,

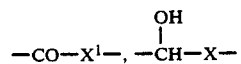

and $-X-CO-$, in which

X is a single bond or lower alkylene and
$X^1$ is lower alkylene, and
a heavy solid line means a single or a double bond.

The object compound or its salt can be prepared by processes as illustrated in the following reaction schemes.

Process 1

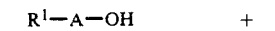

[II]
or its reactive derivative
or a salt thereof

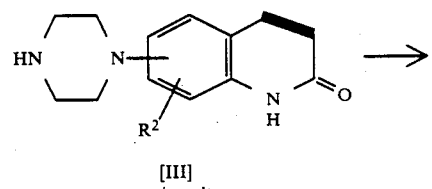

[III]
or its salt

[I]
or its salt

Process 2

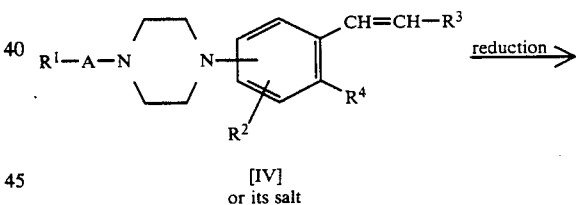

[IV]
or its salt

[I]
or its salt

Process 3

[Ia]
or its salt

-continued
Process 3

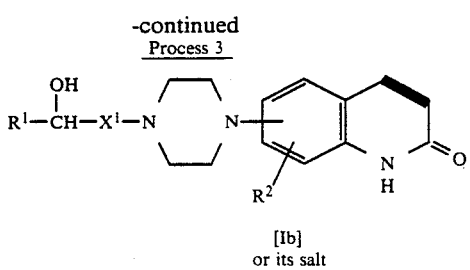

[Ib]
or its salt wherein
R³ is carboxy, esterified carboxy or acyloxycarbonyl,
R⁴ is nitro, hydroxyamino or nitroso, and
R¹, R², X¹, A and a heavy solid line are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "lower alkoxy", "lower alkylthio" and "lower alkylamino" may be a straight or branched one such as methyl, ethyl, propyl, isopropyl, butyl, isobutyl, tert-butyl, pentyl, hexyl or the like, in which the preferable one is $C_1$-$C_4$ alkyl.

Suitable "halogen" may be fluoro, chloro, bromo and iodo.

Suitable "ar(lower)alkoxy" may be substituted or unsubstituted mono- or di- or tri- phenyl(lower)alkoxy, for example, benzyloxy, phenethyloxy, benzhydryloxy, nitrobenzyloxy, tolylmethoxy and the like.

Suitable "acylamino" may be lower alkanoylamino [e.g. formylamino, acetylamino, propionylamino, butyrylamino, isobutyrylamino, valerylamino, isovalerylamino, etc.], lower alkoxycarbonylamino [e.g. methoxycarbonylamino, ethoxycarbonylamino, propoxycarbonylamino, isopropoxycarbonylamino, butoxycarbonylamino, tert-butoxycarbonylamino, etc.], lower alkylsulfonylamino [e.g. mesylamino, ethylsulfonylamino, propylsulfonylamino, etc.], arylsulfonylamino [e.g. phenylsulfonylamino, tosylamino, etc.] or the like.

Suitable "lower alkylene" may be a straight or branched one such as methylene, ethylene, trimethylene, methylethylene, tetramethylene, pentamethylene, hexamethylene or the like, in which the preferable one is $C_1$-$C_4$ alkylene.

Suitable ester moiety in the term "esterified carboxy" may be lower alkyl ester [e.g. methyl ester, ethyl ester, propyl ester, isopropyl ester, butyl ester, isobutyl ester, hexyl ester, etc.], lower alkenyl ester [e.g. vinyl ester, allyl ester, etc.], lower alkynyl ester [e.g. ethynyl ester, propargyl ester, etc.], lower cycloalkyl ester [e.g. cyclopropyl ester, cyclobutyl ester, cyclohexyl ester, etc.], lower cycloalkenyl ester [e.g. cyclobutenyl ester, cyclopentenyl ester, cyclohexenyl ester, etc.], aromatic ester [e.g. phenyl ester, naphthyl ester, thienyl ester, furanyl ester, etc.], ar(lower)alkyl ester [e.g. benzyl ester, phenethyl ester, nitrobenzyl ester, thenyl ester, furfuryl ester, etc.] and the like.

Suitable "acyl" in the term "acyloxycarbonyl" may be an aliphatic acyl, an aromatic acyl [e.g. benzoyl, naphthoyl, etc.], a heterocyclic acyl [e.g. thenoyl, furoyl, etc.] and the like.

The aliphatic acyl may be saturated or unsaturated, acyclic or cyclic ones, such as lower alkanoyl [e.g. formyl, acetyl, propionyl, butyryl, isobutyryl, valeryl, isovaleryl, pivaloyl, hexanoyl, etc.], lower alkanesulfonyl [e.g. mesyl, ethanesulfonyl, propanesulfonyl, etc.], lower alkoxycarbonyl [e.g. methoxycarbonyl, ethoxycaronyl, propoxycarbonyl, isopropoxycarbonyl, butoxycarbonyl, tert-butoxycarbonyl, etc.] or the like.

Suitable ester moiety in the term "di-esterified phosphono" can be referred to the ester moiety as exemplified for "esterified carboxy".

In this respect, the ester group of the di-esterified phosphono may be the same or different.

Suitable "substituted phosphonium salt" can be referred to the phosphonium salt conventionally used in the Wittig reaction [e.g. triphenylphosphonium bromide, tri(n-butyl)phosphonium chloride, etc.].

Suitable "imidazopyridyl" may be imidazo[1,2-a]pyridyl, imidazo[1,5-a]pyridyl, 1H-imidazo[4,5-b]pyridyl, 1H-imidazo[4,5-c]pyridyl, 2H-imidazo[4,5-b]pyridyl, 2H-imidazo[4,5-c]pyridyl, 3H-imidazo[4,5-b]pyridyl, 3H-imidazo[4,5-c]pyridyl, 4H-imidazo[4,5-b]pyridyl, 4H-imidazo[4,5-c]pyridyl, 5H-imidazo[4,5-b]pyridyl, 5H-imidazo[4,5-c]pyridyl, 6H-imidazo[4,5-b]pyridyl, 6H-imidazo[4,5-c]pyrdiyl, 7H-imidazo[4,5-b]pyridyl and 7H-imidazo[4,5-c]pyridyl.

Suitable pharmaceutically acceptable salts of the object compound [I] are conventional non-toxic salts and include an inorganic base salt such as an alkali metal salt [e.g. sodium salt, potassium salt, etc.], an alkaline earth metal salt [e.g. calcium salt, magnesium salt, etc.] aluminum salt, an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], an addition salt with an acidic amino acid [e.g. aspartic acid salt, glutamic acid salt, etc.], and the like.

With respect to the 2(1H)-quinolinone compounds [I] of this invention, it is to be understood that there may be optical isomers due to asymmetric carbon atom(s), and such isomers are also included within the scope of this invention.

The processes for preparing the object compounds [I] of the present invention are explained in detail in the following.

PROCESS 1

The object compound [I] or its salt can be prepared by reacting a compound [II] or its reactive derivative or a salt thereof with a compound [III] or its salt.

The present process is carried out by two ways.

When A in the compound [II] is —X—CO—:

Suitable salts of the compound [II] and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound [I].

Suitable salts of the compound [III] can be referred to the acid addition salts as exemplified for the compound [I].

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as cyanomethyl ester, methoxymethyl ester, p-nitrophenyl ester, 2,4-dinitrophenyl ester, pentachlorophenyl ester, phenylazophenyl ester, carboxymethylthio ester and N-hydroxysuccinimide ester. The kind of such reactive derivatives can be selected depending on the kind of acyl group to be introduced.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction.

In case that the compound [II] is used in the free acid form or salt form, it is preferable to carry out the reaction in the presence of a conventional condensing agent such as N,N'-dicyclohexylcarbodiimide; N-ethyl-N'-(3-dimethylaminopropyl)carbodiimide; N,N'-carbonylbis-(2-methylimidazole); ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, oxalyl chloride, etc.; or the like.

The reaction temperature is not critical and the reaction can be carried out under cooling, at ambient temperature, or under heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

When A in the compound [II] is single bond, —CO—X¹— or

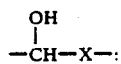

As suitable said reactive derivatives, there may be mentioned an acid residue compound such as halide [e.g. chloride, bromide, fluoride and iodide], sulfonate [e.g. mesylate, tosylate, phenylsulfonate, etc.] or the like.

As suitable examples of the salts of the compound [II], there may be mentioned the same kinds of salt as given for the compound [I].

This reaction is usually carried out in a conventional solvent such as water, an alcohol [e.g. methanol, ethanol, isopropyl alcohol, etc.], dioxane, tetrahydrofuran, N,N-dimethylformamide, methylene chloride, chloroform, tetrachloromethane, or any other conventional solvent which does not adversely affect this reaction, or a mixture thereof.

The reaction is carried out at ambient temperature, under warming or under heating, although the reaction temperature is not critical.

This reaction can also be conducted in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

This reaction can also be performed in the presence of an alkali metal halide such as sodium iodide or potassium iodide.

PROCESS 2

The object compound [I] or its salt can be prepared by subjecting a compound [IV] or its salt to reduction.

Suitable salts of the compound [IV] can be referred to the ones as exemplified for the compound [II] in Process 1 when A in the compound [II] is —X—CO—.

The present reduction is carried out by chemical reduction, catalytic reduction, or the like.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming.

In the present reaction, a compound of the formula:

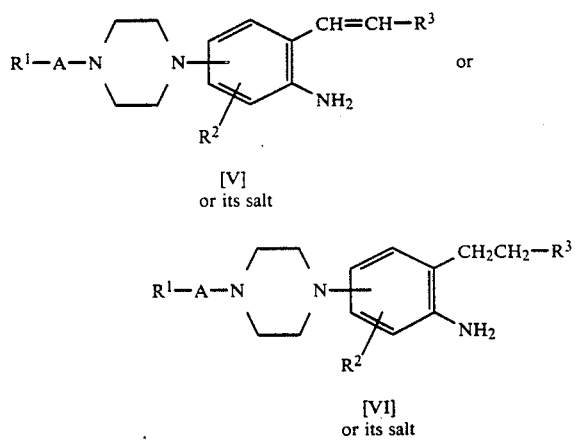

[V]
or its salt

[VI]
or its salt wherein R¹, R², R³ and A are each as defined above, may be obtained according to reaction conditions and the kind of R³ and in that case, the compound [V] or [VI] or a salt thereof is further subjected to lactam formation reaction to give the compound [I] or its salt.

This case is also included within the scope of the present reaction.

Suitable salts of the compounds [V] or [VI] can be referred to the ones as exemplified for the compound [IV].

The present lactam formation reaction is preferably carried out in the presence of an acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, etc.].

The reaction is usually carried out in a solvent such as water, an alcohol [e.g. methanol, ethanol, etc.], dioxane, a mixture thereof or any other solvent which does not adversely influence the reaction. A liquid acid can be also used as the solvent. The reaction temperature is not critical and the reaction is usually carried out under warming to heating.

PROCESS 3

The object compound [Ib] or its salt can be prepared by subjecting a compound [Ia] or its salt to reduction.

Suitable salts of the compounds [Ia] and [Ib] can be referred to the ones as exemplified for the compound [I].

The reduction is preferably carried out by chemical reduction.

Suitable reducing agents to be used in the present reduction are a metal hydride compound such as aluminum hydride compound [e.g. lithium tri-t-butoxyaluminum hydride, etc.], borohydride compound [e.g. sodium borohydride, etc.], aluminum alkoxide [e.g. aluminum isopropoxide, etc.] or the like.

The reaction is usually carried out in a conventional solvent, such as water, alcohol, [e.g. methanol, ethanol, propanol, isopropanol, etc.], chloroform, or any other organic solvent which does not adversely influence the reaction, or a mixture thereof.

The reaction temperature is not critical, and the reaction can be carried out under cooling to heating.

The starting compound [IV] is novel and can be prepared by the following processes.

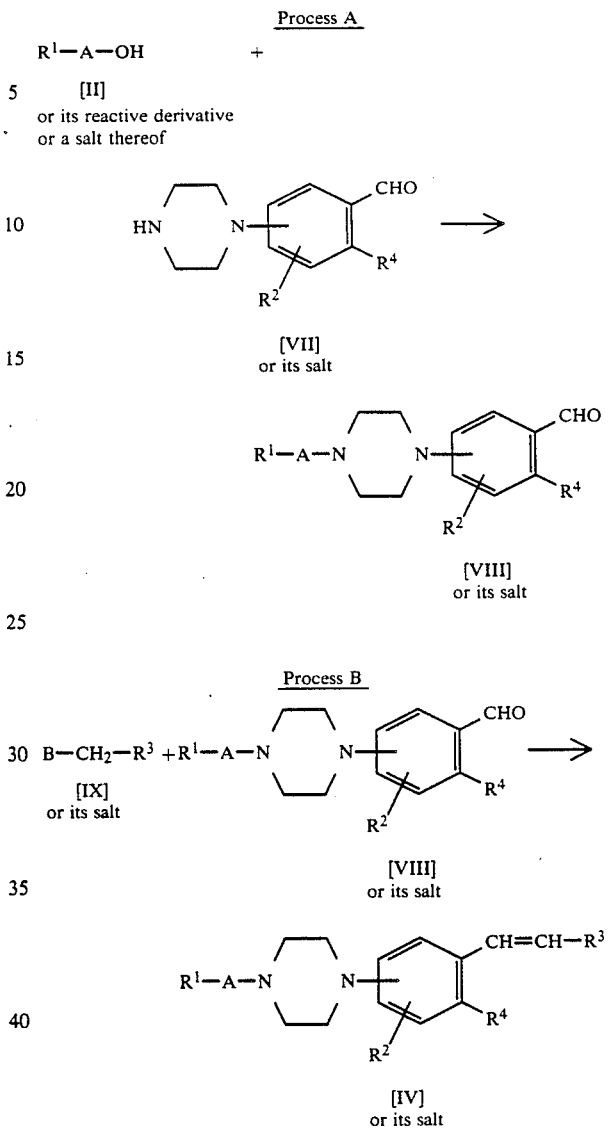

Process A

R¹—A—OH +

[II]
or its reactive derivative
or a salt thereof

[VII]
or its salt

[VIII]
or its salt

Process B

B—CH₂—R³ + R¹—A—N

[IX]
or its salt

[VIII]
or its salt

[IV]
or its salt wherein
B is carboxy, esterified carboxy, di-esterified phosphono or substituted phosphonium salt, and
R¹, R², R³, R⁴ and A are each as defined above.

The above-mentioned processes for preparing the starting compound [IV] are explained in detail in the following.

PROCESS A

The compound [VIII] or its salt can be prepared by reacting a compound [II] or its reactive derivative or a salt thereof with a compound [VII] or its salt.

Suitable salts of the compound [II] and its reactive derivative and suitable said reactive derivatives are explained in Process 1.

Suitable salts of the compound [VII] can be referred the acid addition salts as exemplified for the compound [I].

Suitable salts of the compound [VIII] may be the same as those exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

PROCESS B

The compound [IV] or its salt can be prepared by reacting a compound [IX] or its salt with a compound VIII] or its salt.

Suitable salts of the compound [IX] can be referred to a base salt as exemplified for the compound [II] in Process 1 when A in the compound [II] is —X—CO—.

Suitable salts of the compounds [IV] and [VIII] can be referred to the ones as exemplified for the compound [I].

This reaction is preferably carried out in the presence of an inorganic or organic base such as an alkali metal [e.g. sodium, potassium, etc.], an alkaline earth metal [e.g. magnesium, calcium, etc.], the hydroxide or carbonate thereof, alkali metal hydride [e.g. sodium hydride, etc.], alkali metal amide [e.g. sodium amide, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], lower alkyl alkali metal [e.g. n-butyl lithium, etc.], trialkylamine [e.g. trimethylamine, triethylamine, etc.], pyridine, piperidine, picoline, 1,5-diazabicyclo[4,3,0] non-5-ene, 1,4-diazabicyclo[2,2,0] octane, 1,8-diazabicyclo[5,4,0] undec-7-ene, or the like.

The reaction is usually carried out in a solvent such as water, an alcohol [e.g. methanol, ethanol, etc.], chloroform, methylene chloride, nitromethane, benzene, tetrahydrofuran, diethyl ether, N,N-dimethylformamide, dimethylsulfoxide or any other organic solvent which does not adversely influence the reaction.

The reaction temperature is not critical, and the reaction can be carried out under cooling to heating.

The compounds obtained by the above processes are isolated and purified by a conventional method such as pulverization, recrystallization, column chromatography, reprecipitation or the like.

The new 2(1H)-quinolinone compounds [I] and pharmaceutically acceptable salts thereof possess cardiotonic and hypotensive activities and the capability of reducing heart rate, and are useful for a therapeutic treatment and/or prevention of heart diseases [e.g. cardiac insufficiency, mitral valvular disease, atrial fibrilation, atrial flutter, paroxysmal atrial tachycardia, etc.], hypertension and the like. Additionally, the object compound [I] of this invention is expected to be useful as therapeutic and/or preventive agent for peripheral circular diseases, arrhythmia, angina pectoris, myocardiopathy and the like.

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, suppositories, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

In order to illustrate the usefulness of the object compound [I], the pharmacological test data of some representative compounds of the compound [I] are shown in the following.

Test Compounds (a) 6-[4-(7-Methylimidazo[1,2-a]pyridine-2-carbonyl)-1-piperazinyl]-3,4-dihydro-2(1H)-quinolinone
(b) 6-[4-(5-Methylimidazo[1,2-a]pyridine-2-carbonyl)-1-piperazinyl]-3,4-dihydro-2(1H)-quinolinone
(c) 6-[4-{2-(2-Methyl-4-thiazolyl)acetyl}-1-piperazinyl]-2(1H)-quinolinone
(d) 6-[4-(1,2,3,4-Tetrahydro-2-oxoquinoline-6-carbonyl)-1-piperazinyl]-2(1H)-quinolinone Test 1

Test Method

Mongrel dogs of either sex were anesthetized with sodium pentobarbital, 35 mg/kg, i.p.. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure, from which dp/dt max was derived by analog computing. The measure the systemic blood pressure the left femoral artery was connulated. The blood pressure pulse was used to trigger a heart rate meter. Another catheter was positioned in the vena cave through right femoral vein for injection of drugs. Systemic blood pressure, left ventricular pressure, dp/dt max and heart rate were recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max change (dp/dt M.C.) calculated by following formula.

$$dp/dt\ M.C.\ (\%) = \left( \frac{dp/dt\ \text{max after dosing}}{dp/dt\ \text{max before dosing}} - 1 \right) \times 100$$

Test Results

| Compound | Dose (mg/kg) | dp/dt M.C. (%) |
|---|---|---|
| (a) | 1.0 | 82 |
| (b) | 0.32 | 54 |
| (c) | 1.0 | 69 |

Text 2

Test Method

Male Hartly strain guinea-pigs, weighing 530–600 g, were killed by bleeding and the heart was removed. An atrial strip was removed and suspended in an organ bath containing 50 ml of Tyrode's solution maintained at 30° C and aerated with a gas mixture of 95% $O_2$–5% $CO_2$. The atrium was connected to a strain gauge under an initial tension of 0.4–0.6 g. After constant motility had been obtained the drug was added to the bath solution and the effect on contractile force and heart rate was observed for 30 min. The effect was expressed as percentage values before and after dosing.

Test Results

| Compound | Concentration (g/ml) | Force (%) | Heart Rate (%) |
|---|---|---|---|
| (a) | $3.2 \times 10^{-5}$ | 30.2 | −7.8 |
| (d) | $3.2 \times 10^{-5}$ | 37.7 | −9.6 |

The following Preparations and Examples are given for the purpose of illustrating the present invention in more

PREPARATION 1

To a solution of 8-chloro-3,4-dihydro-2(1H)-quinolinone (5.08 g) in acetic anhydride (50 ml) was dropwise added a solution of nitric acid (d=1.40, 2.97 g) in acetic acid (20 ml) over the period of 10 minutes with stirring under ice-cooling. The mixture was stirred for 2 hours at ambient temperature and then for 6 hours at 50° C., and was allowed to stand for 60 hours at ambient temperature. The resulting precipitates were collected, washed with acetic anhydride and ethyl acetate successively and dried to give 8-chloro-6-nitro-3,4-dihydro-2(1H)-quinolinone (3.83 g).

mp: 208°–209° C.

IR (Nujol): 3100, 1695, 1685, 1615 cm$^{-1}$

NMR (DMSO-d$_6$, δ): 2.5–2.8 (2H, m), 3.0–3.3 (2H, m), 8.18 (2H, s), 10.17 (1H, s)

PREPARATION 2

The following compounds were obtained according to a similar manner to that of Preparation 1.

(1) 8-Methyl-6-nitro-2(1H)-quinolinone mp: 247°–256° C.

IR (Nujol): 1700, 1660, 1620, 1540 cm$^{-1}$

NMR (CF$_3$COOH, δ): 2.80 (3H, s), 7.20 (1H, d, J=9 Hz), 8.40 (1H, d, J=9 Hz), 8.43 (1H, s), 8.67 (1H, s)

(2) 8-Methyl-6-nitro-3,4-dihydro-2(1H)-quinolinone mp: 238°–241° C.

IR (Nujol): 3220, 1675, 1515 cm$^{-1}$

NMR (DMSO-d$_6$, δ): 2.30 (3H, s), 2.50 (2H, t, J=7 Hz), 2.97 (2H, t, J=7 Hz), 7.90 (2H, s), 9.90 (1H, s)

PREPARATION 3

To a suspension of 8-methyl-6-nitro-3,4-dihydro-2(1H)-quinolinone (25 g), activated charcoal (8 g) and ferric chloride (2.5 g) in ethanol (700 ml) was dropwise added hydrazine monohydrate (30 g) over the period of 20 minutes at 77° C., and the mixture was stirred for 1 hour. Then, to the reaction mixture were added activated charcoal (3 g) and ferric chloride (1.5 g) and was dropwise added hydrazine monohydrate (10 g). After refluxed for 1.5 hours, the reaction mixture was filtered and the insoluble material was washed with ethanol and a mixture of ethanol and chloroform successively. The solvent was evaporated under reduced pressure and the residue was dissolved in chloroform. The organic layer was washed with water, dried over magnesium sulfate and concentrated under reduced pressure to give 6-amino-8-methyl-3,4-dihydro-2(1H)-quinolinone (19.5 g).

mp: 162°–167° C.

IR (Nujol): 3500–3100, 1660, 1620 cm$^{-1}$

NMR (CF$_3$COOH, δ): 2.40 (3H, s), 2.70–3.30 (4H, m), 7.23 (2H, s)

PREPARATION 4

The following compounds were obtained according to a similar manner to that of Preparation 3.

(1) 6-Amino-8-chloro-3,4-dihydro-2(1H)-quinolinone mp: 171°–173° C. (dec.)

IR (Nujol): 3400, 3300, 1655, 1620, 1575 cm$^{-1}$

NMR (DMSO-d$_6$, δ): 2.2–2.5 (2H, m), 2.6–2.9 (2H, m), 6.17 (2H, br s), 6.44 (1H, d, J=2 Hz), 6.50 (1H, d, J=2 Hz), 8.98 (1H, s)

(2) 6-Amino-8-methyl-2(1H)-quinolinone mp: 110°–115° C.

IR (Nujol): 3500–3100, 1660, 1620, 1605, 1570 cm$^{-1}$

NMR (CF$_3$COOH, δ): 2.80 (3H, s), 7.30 (1H, d, J=9 Hz), 7.80 (1H, s), 7.97 (1H, s), 8.43 (1H, d, J=9 Hz)

PREPARATION 5

A mixture of 6-amino-8-methyl-3,4-dihydro-2(1H)-quinolinone (19.4 g), bis(2-bromoethyl)amine hydrobromide (41 g) and methanol (140 ml) was stirred for 13 hours at 64° C. After cooling, sodium carbonate (5.83 g) was added thereto and the mixture was stirred for 9 hours at 70° C. After cooling, the resulting precipitate was collected by filtration and the residue was washed with methanol to give 3,4-dihydro-8-methyl-6-(1-piperazinyl)-2(1H)-quinolinone hydrobromide (21.6 g).

mp: >250° C.

IR (Nujol): 1680, 1595 cm$^{-1}$

PREPARATRION 6

The following compounds were obtained according to a similar manner to that of Preparation 5.

(1) 8-Chloro-6-(1-piperazinyl)-3,4-dihydro-2(1H)-quinolinone hydrobromide mp: >250° C.

IR (Nujol): 1655, 1640, 1605, 1575 cm$^{-1}$ (2) 8-Methyl-6-(1-piperazinyl)-2(1H)-quinolinone hydrobromide mp: >250° C.

IR (Nujol): 3200, 1660, 1615, 1600 cm$^{-1}$

PREPARATION 7

A mixture of 2-amino-4-ethylpyridine (3.8 g), ethyl 3-bromo-2-oxopropionate (6.84 g) and ethanol (30 ml) was refluxed for 6 hours. After the reaction mixture was concentrated, water (30 ml) and ehtyl acetate (30 ml) were added to the residue. The mixture was made basic with an aqueous solution of potassium carbonate, and the separated organic layer was washed with brine and dried over magnesium sulfate. The solvent was evaporated and the residue was subjected to a column chromatography on silica gel (150 g) and eluted with 15% solution of ethyl acetate in chloroform. The fractions containing the object compound were combined and concentrated to give ethyl 7-ethylimidazo[1,2-a]pyridine-2-carboxylate (1.26 g).

mp: 102°–103° C.

IR (Nujol): 3120, 1715, 1650 cm$^{-1}$

NMR (DMSO-d$_6$, δ): 1.26 (3H, t, J=7.5 Hz), 1.37 (3H, t, J=7.5 Hz), 2.72 (2H, q, J=7.5 Hz), 4.38 (2H, q, J=7.5 Hz), 6.97 (1H, dd, J=2 Hz, 7 Hz), 7.45 (1H, br s), 8.4–8.7 (2H, m)

PREPARATION 8

The following compounds were obtained according to a similar manner to that of Preparation 7.

(1) Methyl 7-carbamoylimidazo[1,2-a]pyridine-2-carboxylate mp: 250°–251° C. (dec.)

(Nujol): 3440, 3300, 3200, 1730, 1680, 1610 cm$^{-1}$

NMR (DMSO-d$_6$, δ): 3.84 (3H, s), 7.40 (1H, dd, J=1 Hz, 7 Hz), 8.2 (2H, br s), 8.5–8.7 (3H, m)

Mass (m/e): 219 (M$^+$)

(2) Ethyl 8-(2-methylbenzyloxy)imidazo[1,2-a]pyridine-2-carboxylate mp: 158°–159° C.

IR (Nujol): 1710, 1540, 1290 cm$^{-1}$

NMR (DMSO-d$_6$, δ): 1.31 (3H, t, J=7 Hz), 2.38 (3H, s), 4.35 (2H, q, J=7 Hz), 5.30 (2H, s), 6.9–7.1 (2H, m), 7.3–7.7 (4H, m), 8.1–8.4 (1H, m), 8.58 (1H, s)

(3) Ethyl 8-ethylimidazo[1,2-a]pyridine-2-carboxylate

NMR (DMSO-d$_6$, δ): 1.1–1.5 (6H, m), 2.92 (2H, q, J=7.5 Hz), 4.30 (2H, q, J=7.5 Hz), 6.88 (1H, t, J=7 Hz), 7.08 (1H, d, J=7 Hz), 8.40 (1H, d, J=7 Hz), 8.50 (1H, s)

(4) Ethyl 7-methoxyimidazo[1,2-a]pyridine-2-carboxylate mp: 139°–140° C.

IR (Nujol): 1720, 1645, 1550 cm$^{-1}$

NMR (DMSO-d$_6$, δ): 1.33 (3H, t, J=7 Hz), 3.88 (3H, s), 4.27 (2H, q, J=7 Hz), 6.77 (1H, dd, J=2 Hz, 7 Hz), 7.00 (1H, d, J=2 Hz), 8.40 (1H, s), 8.46 (1H, d, J=7 Hz)

(5) Ethyl 7-isopropylimidazo[1,2-a]pyridine-2-carboxylate mp: 67°–68° C.

IR (Nujol): 1720, 1650 cm$^{-1}$

NMR (CDCl$_3$, δ): 1.23 (6H, d, J=7 Hz), 1.40 (3H, t, J=7.5 Hz), 2.6–3.1 (1H, m), 4.34 (2H, q, J=7.5 Hz), 6.67 (1H, dd, J=1.5 Hz, 7 Hz), 7.40 (1H, d, J=1.5 Hz), 8.0 (1H, d, J=7 Hz), 8.05 (1H, s)

(6) Ethyl 7,8-dimethylimidazo[1,2-a]pyridine-2-carboxylate mp: 106°–107° C.

IR (Nujol): 1725, 1635, 1520 cm$^{-1}$

NMR (CDCl$_3$, δ): 1.43 (3H, t, J=7.5 Hz), 2.30 (3H, s), 2.55 (3H, s), 4.32 (2H, q, J=7.5 Hz), 6.62 (1H, d, J=8 Hz), 7.88 (1H, d, J=8 Hz), 8.06 (1H, s)

(7) Ethyl 8-aminoimidazo[1,2-a]pyridine-2-carboxylate mp: 80°–82° C.

IR (Nujol): 3410, 3340, 1720, 1615, 1560 cm$^{-1}$

NMR (DMSO-d$_6$, δ): 1.33 (3H, t, J=7.5 Hz), 4.30 (2H, q, J=7.5 Hz), 5.6 (2H, br s), 6.31 (1H, d, J=9 Hz), 6.5–6.8 (1H, m), 7.79 (1H, d, J=9 Hz), 8.40 (1H, s)

(8) Ethyl 5-ethylimidazo[1,2-a]pyridine-2-carboxylate mp: 94°–96° C.

IR (Nujol): 1725, 1645, 1550 cm$^{-1}$ (9) Ethyl 5,8-dimethylimidazo[1,2-a]pyridine-2-carboxylate mp: 124°–126° C.

IR (neat): 1720, 1690, 1660 cm$^{-1}$

NMR (CDCl$_3$, δ): 1.43 (3H, t, J=7.5 Hz), 2.56 (3H, s), 2.62 (3H, s), 4.48 (2H, q, J=7.5 Hz), 6.57 (1H, d, J=7 Hz), 6.97 (1H, d, J=7 Hz), 8.05 (1H, s)

PREPARATION 9

To a mixture of methyl 2-amino-4-methylthiazole-5-carboxylate (3.72 g) and pyridine (25 ml) was added mesyl chloride (1.6 ml) over the period of 5 minutes under cooling with stirring, and the mixture was stirred for 1 hour at ambient temperature and for 3 hours for 40° C. After the reaction mixture was concentrated, ethyl acetate (50 ml) and tetrahydrofuran (20 ml) were added to the residue and the mixture was adjusted to pH 3 with diluted hydrochloric acid. The separated organic layer was washed with brine, dried over magnesium sulfate and concentrated. The residue was pulverised with diethyl ether to give methyl 2-mesylamino-4-methylthiazole-5-carboxylate (3.5 g).

mp: 216°–218° C.

IR (Nujol): 3150, 3100, 1705, 1610, 1515, 1500 cm$^{-1}$

NMR (DMSO-d$_6$, δ): 2.46 (3H, s), 2.98 (3H, s), 3.80 (3H, s)

PREPARATION 10

To a suspension of methyl 7-carbamoylimidazo[1,2-a]-pyridine-2-carboxylate (1.5 g), methylene chloride (30 ml) and pyridine (2.7 g) was dropwise added trifluoroacetic anhydride (3.6 g) over the period of 5 minutes under cooling with stirring, and the mixture was stirred for 30 minutes at the same temperature. The reaction mixture was poured into ice water (30 ml) and extracted with 5% solution of methanol in chloroform. The organic layer was dried over magnesium sulfate and concentrated. The residue was subjected to a column chromatography on silica gel (50 g) and eluted with 20% solution of methanol in chloroform. The fractions containing the object compound were combined and concentrated to give methyl 7-cyanoimidazo[1,2-a]pyridine-2-carboxylate (0.4 g).

mp: 273°–275° C. (dec.)

IR (Nujol): 2220, 1720, 1530 cm$^{-1}$

NMR (DMSO-d$_6$, δ): 3.84 (3H, s), 7.26 (1H, dd, J=2 Hz, 7 Hz), 8.37 (1H, s), 8.70 (1H, s), 8.72 (1H, d, J=7 Hz)

PREPARATION 11

To a solution of ethyl 7-ethylimidazo[1,2-a]pyridine-2-carboxylate (1.1 g) in ethanol (6 ml) and water (6 ml) was added sodium hydroxide (806 mg) at ambient temperature, and the mixture was stirred for 1 hour. The reaction mixture was adjusted to pH 3.0 with conc. hydrochloric acid. After evaporation of ehtanol, the residual crystal was collected, washed with cold water and dried to give 7-ethylimidazo[1,2-a]pyridine-2-carboxylic acid (0.77 g).

mp: 201°–204° C. (dec.)

IR (Nujol): 1690, 1680, 1610, 1530 cm$^{-1}$

NMR (DMSO-d$_6$, δ): 1.23 (3H, t, J=7 Hz), 2.73 (2H, q, J=7 Hz), 6.95 (1H, dd, J=2 Hz, 7 Hz), 7.43 (1H, d, J=2 Hz), 8.44 (1H, s), 8.53 (1H, d, J=7 Hz)

PREPARATION 12

The following compounds were obtained according to a similar manner to that of Preparation 11.

(1) 8-(2-Methylbenzyloxy)imidazo[1,2-a]pyridine-2-carboxylic acid mp: 236°–237° C.

IR (Nujol): 1690, 1540 cm$^{-1}$

NMR (DMSO-d$_6$, δ): 2.40 (3H, s), 5.30 (2H, s), 6.9–7.1 (2H, m), 7.2–7.7 (4H, m), 8.2–8.4 (1H, m), 8.48 (1H, s)

(2) 8-Ethylimidazo[1,2-a]pyridine-2-carboxylic acid mp: 200°–203° C.

IR (Nujol): 1710, 1690, 1640, 1610 cm$^{-1}$

NMR (D$_2$O+DCl, δ): 1.41 (3H, t, J=7.5 Hz), 3.06 (2H, q, J=7.5 Hz), 7.57 (1H, t, J=7 Hz), 7.97 (1H, d, J=7 Hz), 8.56 (1H, d, J=7 Hz), 8.72 (1H, s)

(3) 7-Methoxyimidazo[1,2-a]pyridine-2-carboxylic acid mp: 225°–227° C. (dec.)

IR (Nujol): 1680, 1600, 1580 cm$^{-1}$

NMR (D$_2$O+DCl, δ): 4.08 (3H, s), 7.1–7.3 (2H, m), 8.52 (1H, s), 8.58 (1H, d, J=7 Hz)

(3) 7-Isopropylimidazo[1,2-a]pyridine-2-carboxylic acid mp: 208°–210° C.

IR (Nujol): 3500, 1660, 1610, 1590, 1525 cm$^{-1}$

NMR (D$_2$O+DCl, δ): 1.38 (6H, d, J=7 Hz), 3.0–3.4 (1H, m), 7.53 (1H, d, J=7 Hz), 7.77 (1H, s), 8.63 (1H, s), 8.66 (1H, d, J=7 Hz)

(5) 7,8-Dimethylimidazo[1,2-a]pyridine-2-carboxylic acid mp: 240°–241° C.

IR (Nujol): 1700, 1630, 1520 cm$^{-1}$

NMR (D$_2$O+DCl, δ): 2.48 (3H, s), 2.54 (3H, s), 7.40 (1H, d, J=7 Hz), 8.48 (1H, d, J=7 Hz), 8.56 (1H, s)

(6) 5,8-Dimethylimidazo[1,2-a]pyridine-2-carboxylic acid mp: 260°–265° C. (dec.)

IR (Nujol): 1720, 1645, 1610, 1585 cm$^{-1}$

NMR (D$_2$O+DCl, δ): 2.63 (3H, s), 2.81 (3H, s), 7.33 (1H, d, J=7.5 Hz), 7.81 (1H, d, J=7.5 Hz), 8.67 (1H, s)

(7) 5-Ethylimidazo[1,2-a]pyridine-2-carboxylic acid mp: 224°–227° C. (dec.)

IR (Nujol): 1720, 1635, 1595, 1530 cm$^{-1}$

NMR (D$_2$O+DCl, δ): 1.48 (3H, t, J=8 Hz), 3.21 (2H, q, J=8 Hz), 7.4–8.3 (3H, m), 8.77 (1H, s)

(8) 7-Cyanoimidazo[1,2-a]pyridine-2-carboxylic acid mp: >250° C.

IR (Nujol): 2240, 1690, 1520 cm$^{-1}$

NMR (D$_2$O+DCl, δ): 7.74 (1H, d, J=7.5 Hz), 8.53 (1H, s), 8.82 (1H, s), 8.90 (1H, d, J=7.5 Hz)

(9) 2-Mesylamino-4-methylthiazole-5-carboxylic acid mp: 169°–171° C.

IR (Nujol): 3170, 2670, 2550, 1685, 1650, 1605 cm$^{-1}$

NMR (DMSO-d$_6$, δ): 2.43 (3H, s), 2.97 (3H, s),

MASS (M/e): 236 (M+)

PREPARATION 13

A mixture of methyl 6-aminonicotinate (510 mg), chloroacetone (620 mg) and ethanol (10 ml) was refluxed for 10 hours. After the solvent was removed, ethanol (5 ml) and water (5 ml) was added to the residue. To the solution containing methyl 2-methylimidazo[1,2-a]pyridine-6-carboxylate was added sodium hydroxide (536 mg) and the mixture was stirred for 1 hour at ambient temperature. Ethanol was evaporated and the resulting crystal was collected. A suspension of the obtained crystal in water (3 ml) was adjusted to pH 3.5 with hydrochloric acid, and the residual crystal was collected and dried to give 2-methylimidazo[1,2-a]pyridine-6-carboxylic acid (0.42 g).

mp: 147°–151° C. (dec.)

NMR (DMSO-d$_6$, δ): 2.47 (3H, s), 7.7–8.2 (3H, m), 9.47 (1H, s)

PREPARATION 14

A mixture of ethyl 8-aminoimidazo[1,2-a]pyridine-2-carboxylate (1.8 g), acetic anhydride (1.6 ml) and tetrahydrofuran (50 ml) was refluxed for 3 hours. The reaction mixture was concentrated with neutralized with a saturated aqueous solution of sodium bicarbonate and the insoluble material was collected and washed with water. To the obtained residue were added water (10 ml) and ethanol (10 ml), and then sodium hydroxide (634 mg) was added thereto at ambient temperature. The mixture was stirred for 50 minutes at ambient temperature and neutralized with conc. hydrochlloric acid under cooling. The residual crystal was collected, washed with water and dried to give 8-acetamidoimidozo[1,2-a]pyridine-2-carboxylic acid (786 mg).

mp: 240°–242° C. (dec.)

IR (Nujol): 3380, 1720, 1695, 1560, 1505 cm$^{-1}$

NMR (DMSO-d$_6$, δ): 2.20 (3H, s), 6.90 (1H, t, J=7.5 Hz), 7.94 (1H, d, J=7.5 Hz), 8.24 (1H, d, J=7.5 Hz), 8.48 (1H, s), 9.91 (1H, br s)

PREPARATION 15

(1) To ice-cooled carbon disulfide (77 ml) were added anhydrous aluminum chloride (61.2 g) and chloroacetyl chloride (36.5 g), and then 2,3-dihydro-3,3-dimethylindol-2-one (24.6 g) was added thereto. The mixture was stirred for 10 minutes at ambient temperature and for 4 hours at 35° to 40° C. The solvent was removed by decantation and to the residue was added ice-water. The resulting crystal was collected, washed with water and dried to give 5-chloroacetyl-2,3-dihydro-3,3-dimethylindol-2-one (37.39 g).

mp: 230°–233° C.

IR (Nujol): 1725, 1670, 1610 cm$^{-1}$ (2) To 5-chloroacetyl-2,3-dihydro-3,3-dimethylindol-2-one (35 g) was added pyridine (140 ml) and the mixture was stirred to 1.6 hours at 85° C. After the mixture was cooled to ambient temperature, the crystal was collected by filtration and washed with pyridine and diethyl ether successively to give 1-[2-(2,3-dihydro-3,3-dimethyl-2-oxoindol-5-yl)-2-oxoethyl]pyridinium chloride (44.6 g).

mp: >250° C.

IR (Nujol): 1712, 1665, 1615, 1590 cm$^{-1}$

NMR (D$_2$O, δ): 1.38 (6H, s), 7.20 (1H, d, J=9 Hz), 8.00 (2H, s), 8.00–8.90 (6H, m)

(3) To a solution of sodium hydroxide (14 g) in water (480 ml) was added 1-[2-(2,3-dihydro-3,3-dimethyl-2-oxoindol-5-yl)-2-oxoethyl]pyridinium chloride (44.3 g) and the mixture was stirred for 1.5 hours at 80° to 85° C. After cooling, the reaction mixture was acidified with conc. hydrochloric acid. The residual crystal was collected by filtration, washed with water and dried to give 2,3-dihydro-3,3-dimethyl-2-oxoindole-5-carboxylic acid (21 g).

mp: >250° C.

IR (Nujol): 2300–3200, 1690, 1620 cm$^{-1}$

NMR (DMSO-d$_6$, δ): 1.30 (6H, s), 6.93 (1H, d, 12.53 (1H, s)

PREPARATION 16

A mixture of 7-methylimidazo[1,2-a]pyridine-2-carboxylic acid (10.56 g), 1-hydroxybenzotriazole (8.1 g), 1-ethyl-3-(3-dimethylaminopropyl)carbodiimide hydrochloride (11.46 g) and N,N-dimethylformamide (360 ml) was stirred for 1 hour at ambient temperature. 1-(3-Formyl-4-nitrophenyl)piperazine hydrochloride (16.2 g) and triethylamine (9.1 g) were added thereto and the mixture was stirred for 1 hour. The resulting precipitates were collected, washed with ethyl acetate (100 ml×2) and water (100 ml×2), and dried to give 1-(3-formyl-4-nitrophenyl)-4-(7-methylimidazo[1,2-a]pyridine-2-carbonyl)piperazine (23.0 g).

mp: 215°–216° C. (dec.)

IR (Nujol): 1695, 1605, 1590, 1570, 1530, 1370 cm$^{-1}$

NMR (DMSO-d$_6$, δ): 2.36 (3H, s), 3.4 (4H, br s), 3.4–3.9 (4H, m), 6.84 (1H, dd, J=2 Hz, 6.94 Hz), 7.08 (1H, d, J=2 Hz), 7.22 (1H, d, J=9 Hz), 7.4 (1H, s), 8.09 (1H, d, J=7 Hz), 8.31 (1H, s), 8.48 (1H, d, J=7 Hz), 10.34 (1H, s)

PREPARATION 17

A mixture of 1-(3-formyl-4-nitrophenyl)-4-(7methylimidazo[1,2-a]pyridine-2-carbonyl)piperazine (22.8 g), triethyl phosphonoacetate (15.6 g), sodium hydride (60% dispersion in mineral oil) (2.92 g) and N,N-dimethylformamide (250 ml) were stirred for 5 hours at ambient temperature. Ethyl acetate (250 ml) was added thereto and the resulting precipitates were collected and washed with ethyl acetate (100 ml) to give ethyl 3-[3-[4-(7-methylimidazo[1,2-a]pyridine-2-carbonyl)-1-piperazinyl]-6-nitrophenyl]acrylate (18.70 g).

mp: 256°-258° C. (dec.)

IR (Nujol): 1710, 1705, 1670, 1605, 1590, 1570 cm$^{-1}$

NMR (DMSO-d$_6$, δ): 1.28 (3H, t, J=7.1 Hz), 2.37 (3H, 15 s), 3.6-4.0 (6H, m), 4.22 (2H, q, J=7.1 Hz), 4.4 (2H, br s), 6.61 (1H, d, J=15.7 Hz), 6.84 (1H, dd, J=1.5 Hz, 6.9 Hz), 7.0-7.3 (2H, m), 7.38 (1H, s), 8.0-8.2 (2H, m), 8.32 (1H, s), 8.49 (1H, d, J=6.9 Hz)

EXAMPLE 1

A mixture of 5-methylimidazo[1,2-a]pyridine-2-carboxylic acid (704 mg), 1-hydroxybenzotriazole (648 mg), 1-ethyl-3-(3-dimethylaminopropyl)carbodiimide hydrochloride (917 mg) and N,N-dimethylformamide (25 ml) was stirred for 1 hour at ambient temperature. 1-(1-piperazinyl)-3,4-dihydro-2(1H)-quinolinone (924 mg) was added thereto, and the mixture was stirred for 10 hours at the same temperature. After the solvent was removed, to the residue were added 5% solution of methanol in chloroform (30 ml) and water (20 ml), and the mixture was adjusted to pH 9 with a saturated aqueous solution of potassium carbonate. The separated organic layer was dried over magnesium sulfate and concentrated. The residue was subjected to a column chromatography on silica gel (80 g) and eluted with 10% solution of methanol in chloroform. The fractions containing the desired compound were collected and concentrated. The residual crystal was recrystallized from methanol-ethyl acetate to give 6-[4-(5-methylimidazo[1,2-a]pyridine-2-carbonyl)-1-piperazinyl]-3,4-dihydro-2(1H)-quinolinone (0.8 g).

mp: 238°-240° C. (dec.)

IR (Nujol): 3440, 1650, 1610, 1540 cm$^{-1}$

NMR (D$_2$O+DCl, δ): 2.5-2.8 (2H, m), 2.90 (3H, s), 2.9-3.2 (2H, m), 3.8-4.1 (4H, m), 4.3-4.7 (4H, m), 7.10 (1H, d, J=9 Hz), 7.3-7.7 (2H, m), 7.60 (1H, s), 7.7-8.1 (2H, m), 8.62 (1H, s)

Mass (m/e): 389 (M+)

EXAMPLE 2

A mixture of 2-(2-methyl-4-thiazolyl)acetic acid (628 mg), 1-hydroxybenzotriazole (648 mg), 1-ethyl-3-(3-dimethylaminopropyl)carbodiimide hydrochloride (917 mg) and N,N-dimethylformamide (25 ml) was stirred for 1 hour at ambient temperature. 6-(1-Piperazinyl)-2(1H)-quinolinone (687 mg) and triethylamine (1 ml) were added thereto, and the mixture was stirred for 3 hours at the same temperature. After the reaction mixture was concentrated in vacuo, to the residue were added ethyl acetate (10 ml) and water (10 ml) and the mixture was stirred. The resulting oil was separated by decantation and dissolved in tetrahydrofuran. The solution was washed with brine, dried over magnesium sulfate and concentrated. The residue was subjected to a column chromatography on silica gel (80 g) and eluted with 3% solution of methanol in chloroform. The fractions containing the desired compound were collected and concentrated to give a residue, which was crystallized from ethyl acetate-diethyl ether to give 6-[4-{2-(2-methyl-4-thiazolyl)acetyl}-1-piperazinyl]-2(1H)-quinolinone (0.74 g).

mp: 201°-202° C.

IR (Nujol): 1665, 1640, 1620, 1510, 1500 cm$^{-1}$

NMR (DMSO-d$_6$, δ): 2.60 (3H, s), 2.9-3.2 (4H, m), 3.4-3.8 (4H, m), 3.80 (2H, s), 6.42 (1H, d, J=11 Hz), 7.0-7.3 (4H, m), 7.76 (1H, d, J=11 Hz)

MASS (m/e): 368, 369 (M+)

EXAMPLE 3

The following compounds were obtained according to a similar manner to that of Example 1 or 2.

(1)   6-[4-(5-Methylimidazo[1,2-a]pyridine-2-carbonyl)-1-piperazinyl]-8-chloro-3,4-dihydro-2(1H)-quinolinone mp: 230°-232° C.

IR (Nujol): 1668, 1605, 1580, 1540 cm$^{-1}$

NMR (D$_2$O+DCl, δ): 2.5-2.9 (2H, m), 2.87 (3H, s), 3.0-3.3 (2H, m), 3.8-4.2 (4H, m), 4.2-4.5 (4H, m), 7.40 (1H, d, J=7.5 Hz), 7.63 (1H, d, J=2 Hz), 7.80 (1H, d, J=2 Hz), 7.8-8.2 (2H, m), 8.58 (1H, s)

MASS (m/e): 423, 425 (M+)

(2)   6-[4-(1-Methylindole-2-carbonyl)-1-piperazinyl]-3,4-dihydro-2(1H)-quinolinone mp: 142°-144° C.

IR (Nujol): 1660, 1600, 1510 cm$^{-1}$

NMR (DMSO-d$_6$, δ): 2.3-2.6 (2H, m), 2.7-3.0 (2H, m), 3.0-3.3 (4H, m), 3.78 (3H, s), 3.6-3.9 (4H, s), 6.7-7.0 (4H, m), 7.0-7.4 (2H, m), 7.4-7.7 (2H, m), 9.93 (1H, s)

MASS (m/e): 388 (M+)

(3)   6-[4-(7-Methylimidazo[1,2-a]pyridine-2-carbonyl)-1-piperazinyl]-8-chloro-3,4-dihydro-2(1H)-quinolinone mp: 199°-200° C.

IR (Nujol): 1675, 1630, 1600, 1575 cm$^{-1}$

NMR (D$_2$O+DCl, δ): 2.6-2.9 (2H, m), 2.69 (3H, s), 3.0-3.2 (2H, m), 3.7-4.0 (4H, m), 4.2-4.5 (4H, m), 7.50 (1H, d, J=2 Hz), 7.4-7.6 (2H, m), 7.80 (1H, s), 8.63 (1H, s), 8.65 (1H, d, J=8 Hz)

MASS (m/e): 423 (M+)

(6)   6-[4-(3-Indolecarbonyl)-1-piperazinyl]-3,4-dihydro-2(1H)-quinolinone mp: 268°-269° C. (dec.)

IR (Nujol): 3410, 3210, 1660, 1600, 1530, 1500 cm$^{-1}$

NMR (DMSO-d$_6$, δ): 2.3-2.5 (2H, m), 2.7-3.0 (2H, m), 3.0-3.3 (4H, m), 3.7-4.0 (4H, m), 6.7-6.9 (3H, m), 7.1-7.9 (5H, m), 9.88 (1H, s), 11.65 (1H, br s)

MASS (m/e): 374 (M+)

(5)   6-[4-(2-Indolecarbonyl)-1-piperazinyl]-3,4-dihydro2(1H)-quinolinone mp: 233°-235° C.

IR (Nujol): 3250, 1665, 1595, 1520, 1500 cm$^{-1}$

NMR (DMSO-d$_6$, δ): 2.3-2.5 (2H, m), 2.7-3.0 (2H, m), 3.0-3.3 (4H, m), 3.8-4.1 (4H, m), 6.7-7.0 (3H, m), 7.0-7.8 (5H, m), 9.92 (1H, s), 11.61 (1H, br s)

(6)   6-[4-(5-Methylindole-2-carbonyl)-1-piperazinyl]-3,4-dihydro-2(1H)-quinolinone mp: 165°-167° C.

IR (Nujol): 3280, 3040, 1650, 1610 cm$^{-1}$

NMR (DMSO-d$_6$, δ): 2.34 (3H, s), 2.2-2.5 (2H, m), 2.6-2.9 (2H, m), 2.9-3.3 (4H, m), 3.7-4.0 (4H, m), 6.6-6.9 (4H, m), 6.97 (1H, dd, J=2 Hz, 9 Hz), 7.30 (1H, d, J=9 Hz), 7.36 (1H, s), 9.83 (1H, s), 11.55 (1H, s)

MASS (m/e): 388 (M+)

(7)   6-[4-(2-Methylthiazole-4-carbonyl)-1-piperazinyl]3,4-dihydro-2(1H)-quinolinone mp: 155°-156° C.

IR (Nujol): 3180, 1675, 1605, 1500 cm$^{-1}$

NMR (DMSO-d$_6$, δ): 2.3-3.0 (4H, m), 2.70 (3H, s), 3.0-3.3 (4H, m), 3.6-4.0 (4H, m), 6.78 (3H, s), 7.94 (1H, s), 9.85 (1H, s)

MASS (m/e): 356 (M+)

(8) 6-[4-[2-Amino-4-ethylthiazole-5-carbonyl)-1piperazinyl]-3,4-dihydro-2(1H)-quinolinone
mp: 204°–206° C.
IR (Nujol): 3330, 3270, 3100, 1650, 1605, 1590 cm$^{-1}$
NMR (DMSO-d$_6$, δ): 1.14 (3H, t, J=7 Hz), 2.48 (2H, q, J=7 Hz), 2.3–3.0 (4H, m), 2.9–3.3 (4H, m), 3.5–3.8 (4H, m), 6.79 (3H, s), 7.26 (2H, s), 9.85 (1H, s)
MASS (m/e): 385 (M$^+$)

(9) 6-[4-(2-Benzimidazolecarbonyl)-1-piperazinyl]3,4-dihydro-2(1H)-quinolinone
mp: 291°–294° C. (dec.)
IR (Nujol): 3240, 1670, 1610, 1510 cm$^{-1}$
NMR (DMSO-d$_6$, δ): 2.3–2.6 (2H, m), 2.7–3.0 (2H, m), 3.0–3.3 (4H, m), 3.7–4.0 (2H, br s), 4.5–4.8 (2H, br s), 6.7–6.9 (3H, m), 7.2–7.9 (4H, m), 9.81 (1H, s), 13.14 (1H, br s)
MASS (m/e): 375 (M$^+$)

(10) 6-[4-(2-tert-Butoxycarbonylamino-4-methylthiazole-5-carbonyl)-1-piperazinyl]-3,4-dihydro-2(1H)-quinolinone
mp: 162°–163° C.
IR (Nujol): 3200, 1705, 1655, 1620, 1550, 1505 cm$^{-1}$
NMR (DMSO-d$_6$, δ): 1.50 (9H, s), 2.28 (3H, s), 2.4–2.7 (2H, m), 2.8–3.2 (6H, m), 3.5–3.8 (4H, m), 6.8 (3H, br s), 9.83 (1H, s)

(11) 6-[4-(2-Methylamino-4-ethylthiazole-5-carbonyl)-1-piperazinyl]-3,4-dihydro-2(1H)-quinolinone
mp: 218°–220° C. (dec.)
IR (Nujol): 3330, 3200, 3110, 1665, 1600, 1505 cm$^{-1}$
NMR (DMSO-d$_6$, δ): 1.14 (3H, t, J=7 Hz), 2.40 (2H, q, J=7 Hz), 2.4–2.6 (2H, m), 2.7–2.9 (2H, m), 2.82 (3H, d, J=5 Hz), 3.0 (4H, br s), 3.6 (4H, br s), 6.7–6.9 (3H, m), 8.22 (1H, q, J=5 Hz), 9.94 (1H, s)
MASS (m/e): 399 (M$^+$)

(12) 6-[4-(5-Bromoindole-2-carbonyl)-1-piperazinyl]-8-methyl-2(1H)-quinolinone
mp: >250° C.
IR (Nujol): 1660, 1610, 1595, 1525 cm$^{-1}$
NMR (DMSO-d$_6$, δ): 2.37 (3H, s), 3.17 (4H, m), 3.87 (4H, m), 6.40 (1H, d, J=9 Hz), 6.76 (1H, s), 6.96 (1H, br s), 7.10 (1H, br s), 7.30 (2H, m), 7.73 (1H, d, J=9 Hz), 7.77 (1H, d, J=2 Hz), 0.70 (1H, s), 11.80 (1H, s)

(13) 6-[4-(5-Bromoindole-2-carbonyl)-1-piperazinyl]-8-methyl-3,4-dihydro-2(1H)-quinolinone
mp: 255°–260° C.
IR (Nujol): 1665, 1615, 1595 cm$^{-1}$
NMR (DMSO-d$_6$, δ): 2.16 (3H, s), 2.33 (2H, m), 2.76 (2H, m), 3.10 (4H, m), 3.80 (4H, m), 6.60 (2H, s), 6.76 (1H, s), 7.30 (2H, m), 7.73 (1H, s), 9.13 (1H, s), 11.73 (1H, s)

(14) 6-[4-(5-Chloroindole-2-carbonyl)-1-piperazinyl]-8-methyl-3,4-dihydro-2(1H)-quinolinone
mp: 257°–259° C.
Nujol): 1665, 1620, 1530 cm$^{-1}$
NMR (DMSO-d$_6$, δ): 2.13 (3H, s), 2.33 (2H, m), 2.73 (2H, m), 3.10 (4H, m), 3.80 (4H, m), 6.60 (2H, s), 6.76 (1H, br s), 7.13 (1H, dd, J=2,7 Hz), 7.40 (1H, d, J=7 Hz), 7.60 (1H, d, J=2 Hz), 9.13 (1H, s), 11.73 (1H, s)

(15) 6-[4-(5-Chloroindole-2-carbonyl)-1-piperazinyl]-8-methyl-2(1H)-quinolinone
mp: >250° C.
Nujol): 1660, 1600, 1530 cm$^{-1}$
NMR (DMSO-d$_6$, δ): 2.36 (3H, s), 3.13 (4H, m), 3.83 (4H, m), 6.40 (1H, d, J=9 Hz), 6.76 (1H, s), 6.96 (1H, br s), 7.10 (2H, s), 7.40 (1H, d, J=9 Hz), 7.60 (1H, br s), 7.70 (1H, d, J=9 Hz), 10.70 (1H, s), 11.73 (1H, s)

(16) 6-[4-(1,2,3,4-Tetrahydro-2-oxoquinoline-6-carbonyl)-1-piperazinyl]-8-methyl-2(1H)-quinolinone
mp: >250° C.
IR (Nujol): 1680, 1610, 1505 cm$^{-1}$
NMR (DMSO-d$_6$, δ): 2.37 (3H, s), 2.50 (2H, m), 2.90 (2H, t, J=7 Hz), 3.13 (4H, m), 3.60 (4H, m), 6.43 (1H, d, J=9 Hz), 6.80–7.30 (4H, m), 7.26 (1H, s), 7.76 (1H, d, J=9 Hz), 10.20 (1H, s), 10.70 (1H, s)

(17) 6-[4-(7-Methylimidazo[1,2-a]pyridine-2-carbonyl)-1-piperazinyl]-8-methyl-2(1H)-quinolinone
mp: 231°–234° C.
IR (Nujol): 1660, 1615, 1555, 1515 cm$^{-1}$
NMR (DMSO-d$_6$, δ): 2.33 (3H, s), 2.37 (3H, s), 3.33 (4H, m), 4.00 (4H, m), 6.40 (1H, d, J=8 Hz), 6.67 (1H, dd, J=2, 7 Hz), 6.96 (1H, br s), 7.13 [1H, br s), 7.33 (1H, s) 7.73 (1H, d, J=8 Hz), 8.20 (1H, s), 8.40 (1H, d, J=7 Hz), 10.7 (1H, s)

(18) 6-[4-(7-Methylimidazo[1,2-a]pyridine-2-carbonyl)-1piperazinyl]-8-methyl-3,4-dihydro-2(1H)-quinolinone
mp: 233°–234° C.
IR (Nujol): 1670, 1605, 1550, 1500 cm$^{-1}$
NMR (DMSO-d$_6$, δ): 2.13 (3H, s), 2.30 (3H, s), 2.40 (2H, m), 2.66 (2H, m), 3.03 (4H, m), 4.00 (4H, m), 6.60 (2H, s), 6.76 (1H, d, J=7 Hz), 7.30 (1H, s), 8.20 (1H, s), 8.36 (1H, d, J=7 Hz), 9.33 (1H, s)

(19) 6-[4-(1,2,3,4-Tetrahydro-2-oxoquinoline-6-carbonyl)-1-piperazinyl]-8-methyl-3,4-dihydro-2(1H)-quinolinone
mp: >260° C.
IR (Nujol): 1675, 1630, 1610, 1490 cm$^{-1}$
NMR (DMSO-d$_6$, δ): 2.16 (3H, s), 2.50 (4H, m), 2.80 (4H, m), 3.03 (4H, m), 3.60 (4H, m), 6.60 (2H, s), 6.86 (1H, d, J=7 Hz), 7.26 (1H, d, J=7 Hz), 7.26 (1H, s), 9.16 (1H, s), 10.20 (1H, s)

(20) 6-[4-(1,2,3,4-Tetrahydro-2-oxoquinoline-6-carbonyl)-1-piperazinyl]-3,4-dihydro-2(1H)-quinolinone
mp: 160°–170° C.
IR (Nujol): 1650, 1600 cm$^{-1}$
NMR (CDCl$_3$, δ): 2.0–3.4 (12H, m), 3.5–4.1 (4H, m), 6.7–7.5 (6H, m), 9.38 (1H, s), 9.80 (1H, s)
MASS (m/e): 404 (M$^+$)

(21) 6-[4-(7-Ethylimidazo[1,2-a]pyridine-2-carbonyl)-1-piperazinyl]-3,4-dihydro-2(1H)-quinolinone
mp: 200°–201° C.
IR (Nujol): 1670, 1605, 1550, 1505 cm$^{-1}$
NMR (D$_2$O+DCl, δ): 1.42 (3H, t, J=7.5 Hz), 2.5–2.8 (2H, m), 2.98 (2H, q, J=7 Hz), 3–3.3 (2H, m), 3.8–4.2 (4H, m), 4.2–4.7 (4H, m), 7.03 (1H, d, J=9 Hz), 7.52 (1H, dd, J=2 Hz, 6 Hz), 7.61 (1H, d, J=9 Hz), 7.82 (1H, s), 8.65 (1H, s), 8.67 (1H, d, J=6 Hz)
MASS (m/e): 403 (M$^+$)

(22) 6-[4-(7,8-Dimethylimidazo[1,2-a]pyridine-2-carbonyl)1-piperazinyl]-3,4-dihydro-2(1H)-quinolinone
mp: 234°–235° C.
IR (Nujol): 3210, 1670, 1625, 1550, 1510 cm$^{-1}$
NMR (D$_2$O+DCl, δ): 2.61 (6H, s), 3.4–3.7 (2H, m), 2.9–3.2 (2H, m), 3.7–4.1 (4H, m), 4.2–4.5 (4H, m), 7.08 (1H, d, J=10 Hz), 7.38 (1H, d, J=7.5 Hz), 7.50 (1H, dd, J=2 Hz, 10 Hz), 7.62 (1H, s), 8.55 (1H, d, J=7.5 Hz), 8.61 (1H, s)
MASS (m/e): 403 (M$^+$)

(23) 6-[4-(7-Isopropylimidazo[1,2-a]pyridine-2-carbonyl)-1-piperazinyl]-3,4-dihydro-2(1H)-quinolinone
mp: 200°–201° C.
IR (Nujol): 3180, 3150, 1655, 1600, 1540, 1510 cm$^{-1}$
NMR (D$_2$O+DCl, δ): 1.38 (6H, d, J=7.5 Hz), 2.5–2.7 (2H, m), 2.9–3.4 (3H, m), 3.8–4.1 (4H, m), 4.2–4.5 (4H, m), 7.12 (1H, d, J=10 Hz), 7.5–7.7 (3H, m), 7.83 (1H, s), 8.63 (1H, s), 8.68 [1H, d, J=7 Hz)
MASS (m/e): 417 (M$^+$)

(24) 6-[4-(8-Ethylimidazo[1,2-a]pyridine-2-carbonyl)-1-piperazinyl]-3,4-dihydro-2(1H)-quinolinone
mp: 218°–220° C.
Nujol): 3200, 1670, 1620, 1540, 1500 cm$^{-1}$
NMR (D$_2$O+DCl, δ): 1.45 (3H, t, J=8 Hz), 2.50–2.77 (2H, m), 2.9–3.2 (2H, m), 3.08 (2H, q, J=8 Hz), 3.8–4.2 (4H, m), 4.2–4.6 (4H, m), 7.10 (1H, d, J=9 Hz), 7.55 (1H, t, J=9 Hz), 7.63 (1H, dd, J=2 Hz, 9 Hz), 7.67 (1H, s), 7.95 (1H, d, J=9 Hz), 8.87 (1H, d, J=9 Hz), 8.72 (1H, s).
MASS (m/e): 403 (M$^+$)

(25) 6-[4-(8-Acetamidoimidazo[1,2-a]pyridine-2-carbonyl)-1-piperazinyl]-3,4-dihydro-2(1H)-quinolinone
mp: 303°–306° C. (dec.)
IR (Nujol): 3180, 1670, 1660, 1655, 1615, 1545, 1510 cm$^{-1}$
NMR (DMSO-d$_6$, δ): 2.19 (3H, s), 2.2–2.5 (2H, m), 2.6–2.9 (2H, m), 2.9–3.2 (4H, m), 3.7–4.3 (4H, m), 6.6–7.0 (4H, m), 7.91 (1H, d, J=7.5 Hz), 8.22 (1H, d, J=6 Hz), 8.28 (1H, s), 9.76 (1H, s), 9.83 (1H, s)
MASS (m/e): 432 (M$^+$)

(26) 6-[4-(2-Methylimidazo[1,2-a]pyridine-6-carbonyl)-1-piperazinyl]-3,4-dihydro-2(1H)-quinolinone
mp: 257°–259° C.
IR (Nujol): 1670, 1640, 1605, 1510 cm$^{-1}$
NMR (D$_2$O+DCl, δ): 2.5–2.8 (2H, m), 2.65 (3H, s), 2.9–3.2 (2H, m), 3.7–4.0 (4H, m), 4.0–4.4 (4H, m), 7.06 (1H, d, J=9 Hz), 7.47 (1H, dd, J=2 Hz, 9 Hz), 7.50 (1H, d, J=2 Hz), 7.9–8.2 (3H, m), 9.0 (1H, d, J=1 Hz)
MASS (m/e): 389 (M$^+$)

(27) 6-[4-(2-Methylaminothiazole-4-carbonyl)-1 piperazinyl]-2(1H)-quinolinone
mp: 183°–184° C. (dec.)
IR (Nujol): 3340, 1660, 1620, 1560 cm$^{-1}$
NMR (DMSO-d$_6$, δ): 2.83 (3H, d, J=5 Hz), 3.1 (4H, br s), 3.8 (4H, br s), 6.37 (1H, d, J=10 Hz), 7.0–7.3 (3H, m), 7.40 (1H, s), 7.6–7.9 (2H, m), 11.50 (1H, br s)
MASS (m/e): 369 (M$^+$)

(28) 6-[4-{2-Methylamino-5-(4-pyridyl)thiazole-4-carbonyl}-1-piperazinyl]-3,4-dihydro-2(1H)-quinolinone
mp: 290°–294° C. (dec.)
IR (Nujol): 3200, 1670, 1640, 1610, 1590, 1510 cm$^{-1}$
NMR (DMSO-d$_6$, δ): 2.2–2.5 (2H, m), 2.88 (3H, d, J=5 Hz), 2.6–3.0 (4H, m), 3.1 (2H, br s), 3.3 (2H, br s), 3.8 (2H, br s), 6.13 (3H, s), 7.28, 8.50 (4H, ABq, J=5.1 Hz), 8.18 (1H, q, J=5 Hz), 9.88 (1H, s)
MASS (m/e): 448 (M$^+$)

(29) 6-[4-(2,5-Dimethylthiazole-4-carbonyl)-1-piperazinyl]-3,4-dihydro-2(1H)-quinolinone
mp: 179°–180° C.
IR (Nujol): 3250, 1665, 1625, 1485 cm$^{-1}$
NMR (DMSO-d$_6$, δ): 2.40 (3H, s), 2.3–2.6 (2H, m), 2.58 (3H, s), 2.7 (4H, br s), 2.7–3.0 (2H, m), 3.4–4.0 (4H, m), 6.7–7.1 (3H, m), 8.67 (1H, s)
MASS (m/e): 370 (M$^+$)

(30) 6-[4-(5-Indolecarbonyl)-1-piperazinyl]-3,4-dihydro-2(1H)-quinolinone
mp: 268° C. (dec.)
IR (Nujol): 3150, 1650, 1600, 1500 cm$^{-1}$
NMR (DMSO-d$_6$, δ): 2.3–2.5 (2H, m), 2.7–2.9 (2H, m), 2.9–3.3 (4H, m), 3.4–3.8 (4H, m), 6.47 (1H, d, J=2 Hz), 6.6–6.9 (3H, m), 7.12 (1H, dd, J=2 Hz, 9 Hz), 7.36 (1H, s), 7.42 (1H, d, J=9 Hz), 7.62 (1H, s), 9.80 (1H, s), 11.28 (1H, br s)
MASS (m/e): 374 (M$^+$)

(31) 6-[4-(8-Methylimidazo[1,2-a]pyridine-2-carbonyl)-1-piperazinyl]-2(1H)-quinolinone
mp: 278°–279° C. (dec.)
IR (Nujol): 1675, 1620, 1530, 1500 cm$^{-1}$
NMR (D$_2$O+DCl, δ): 2.68 (3H, s), 4.0–4.3 (4H, br s), 4.3–4.6 (4H, br s), 6.65 (1H, d, J=10 Hz), 7.4–7.6 (2H, m), 7.8–8.1 (4H, m), 8.63 (1H, d, J=8 Hz), 8.70 (1H, s)
MASS (m/e): 387 (M$^+$)

(32) 6-[4-(6-Chloroimidazo[1,2-a]pyridine-2-carbonyl)-1-piperazinyl]-3,4-dihydro-2(1H)-quinolinone
mp: 300°–303° C. (dec.)
IR (Nujol): 3150, 1680, 1625, 1535, 1510 cm$^{-1}$
NMR (D$_2$O+DCl, δ): 2.5–2.8 (2H, m), 2.9–3.2 (2H, m), 3.9–4.2 (4H, m), 4.2–4.6 (4H, m), 7.22 (1H, d, J=9 Hz), 7.63 (1H, dd, J=2 Hz, 9 Hz), 7.68 (1H, d, J=2 Hz), 8.08 (1H, d, J=10 Hz), 8.17 (1H, d, J=10 Hz), 8.80 (1H, s), 9.03 (1H, d, J=2 Hz)

(33) 6-[4-(3,7-Dimethylimidazo[1,2-a]pyridine-2-carbonyl)-piperazinyl]-3,4-dihydro-2(1H)-quinolinone
mp: 206°–208° C.
IR (Nujol): 3180, 1655, 1620, 1555, 1505 cm$^{-1}$
NMR (D$_2$O+DCl, δ): 2.5–2.8 (2H, m), 2.65 (3H, s), 2.77 (3H, s), 2.9–3.2 (2H, m), 3.8–4.2 (4H, m), 4.2–4.6 (4H, m), 7.12 (1H, d, J=9 Hz), 7.52 (1H, d, J=7.5 Hz), 7.59 (1H, d, J=9 Hz), 7.63 (1H, s), 7.80 (1H, s), 8.58 (1H, d, J=7.5 Hz)
MASS (m/e): 403 (M$^+$)

(34) 6-[4-(7-Chloroimidazo[1,2-a]pyridine-2-carbonyl)-1-piperazinyl]-3,4-dihydro-2(1H)-quinolinone
mp: 238°–241° C. (dec.)
IR (Nujol): 3380, 3230, 1665, 1630, 1590, 1545, 1505 cm$^{-1}$
NMR (D$_2$O+DCl, δ): 2.4–2.7 (2H, m), 3.08 (2H, t, J=7.5 Hz), 3.7–4.2 (4H, m), 4.2–4.6 (4H, m), 7.08 (1H, d, J=8 Hz), 7.5–7.8 (3H, m), 8.15 (1H, d, J=2 Hz), 8.76 (1H, s), 8.83 (1H, d, J=8 Hz)
MASS (m/e): 409 (M$^+$)

(35) 6-[4-(7-Cyanoimidazo[1,2-a]pyridine-2-carbonyl)-1-piperazinyl]-3,4-dihydro-2{1H)-quinolinone
mp: 305°–307° C. (dec.)
IR (Nujol): 3180, 3080, 2225, 1670, 1605, 1505 cm$^{-1}$
NMR (DMSO-d$_6$, δ): 2.2–2.6 (2H, m), 2.6–3.0 (2H, m), 3.1 (4H, br s), 3.5–4.3 (4H, m), 6.7 (3H, br s), 7.0–7.3 (1H, m), 8.2–8.8 (3H, m), 9.7 (1H, br s)
MASS (m/e): 400 (M$^+$)

(36) 6-[4-(6-Methylimidazo[1,2-a]pyridine-2-carbonyl)-1-piperazinyl]-3,4-dihydro-2(1H)-quinolinone
mp: 289°–290° C. (dec.)
IR (Nujol): 3140, 1665, 1595, 1560, 1505 cm$^{-1}$
NMR (D$_2$O+DCl, δ): 2.53 (3H, s), 2.5–2.7 (2H, m), 2.9–3.2 (2H, m), 3.8–4.21 (4H, m), 4.3–4.6 (4H, m), 7.10 (1H, d, J=9 Hz), 7.64 (1H, dd, J=2 Hz, 9 Hz), 7.67 (1H, s), 7.8–8.1 (2H, m), 8.62 (1H, s), 8.69 (1H, s)
MASS (m/e): 389 (M$^+$)

(37) 6-[4-(7-Methylimidazo[1,2-a]pyridine-2-carbonyl)-1-piperazinyl]-2(1H)-quinolinone
mp: 299°–301° C. (dec.)
IR (Nujol): 3450, 3340, 1655, 1620, 1590, 1550, 1510 cm$^{-1}$
NMR (DMSO-d$_6$, δ): 2.33 (3H, s), 3.2 (4H, br s), 4.1 (4H, br s), 6.43 (1H, d, J=10 Hz), 6.76 (1H, d, J=7.5 Hz), 7–7.5 (4H, m), 7.75 (1H, d, J=10 Hz), 8.24 (1H, s), 8.41 (1H, d, J=7.5 Hz)
Mass (m/e): 387 (M$^{30}$)

(38) 6-[4-(8-Methylimidazo[1,2-a]pyridine-2-carbonyl)-1-piperazinyl]-3,4-dihydro-2(1H)-quinolinone
mp: 272°–274° C.
IR (Nujol): 3190, 3060, 1670, 1620, 1545 cm$^{-1}$
NMR (D$_2$O+DCl, δ): 2.5–2.7 (2H, m), 2.73 (3H, s), 2.9–3.2 (2H, m), 3.9–4.2 (4H, m), 4.2–4.6 (4H, m), 7.12 (1H, d, J=9 Hz), 7.4–7.6 (2H, m), 7.67 (1H, s), 7.8–8.0 (1H, m), 8.70 (1H, d, J=9 Hz), 8.72 (1H, s)

(39) 6-[4-(5,7-Dimethylimidazo[1,2-a]pyridine-2-carbonyl)-piperazinyl]-3,4-dihydro-2(1H)-quinolinone
mp: 243°–244° C.
IR (Nujol): 3430, 1675, 1645, 1615, 1555 cm⁻¹
NMR (D₂O+DCl, δ): 2.4–2.8 (2H, m), 2.63 (3H, s), 2.7–3.0 (2H, m), 2.84 (3H, s), 2.9–3.2 (4H, m), 3.8–4.5 (4H, m), 6.9–7.2 (3H, m), 7.31 (1H, s), 7.62 (1H, s), 8.42 (1H, s)
MASS (m/e): 403 (M+)

(40) 6-[4-(3-Methyl-6-nitroimidazo[1,5-a]pyridine-1-carbonyl)-1-piperazinyl]-3,4-dihydro-2(1H)-quinolinone
mp: 256°–258° C.
IR (Nujol): 3400, 1685, 1670, 1640, 1590, 1540 1505 cm⁻¹
NMR (DMSO-d₆, δ): 2.25–2.50 (2H, m), 2.6–2.9 (2H, m), 2.74 (3H, s), 3.0–3.4 (4H, m), 3.9–4.3 (4H, m), 6.6–6.9 (3H, m), 7.60 (1H, dd, J=2 Hz, 10 Hz), 8.80 (1H, d, J=10 Hz), 9.30 (1H, s), 9.80 (1H, s)
MASS (m/e): 434 (M+)

(41) 6-[4-(5-Chloroindole-2-carbonyl)-1-piperazinyl]-3,4-dihydro-8-chloro-2(1H)-quinolinone
mp: 249°–250° C.
IR (Nujol): 3180, 1680, 1660, 1625, 1575, 1535 cm⁻¹
NMR (DMSO-d₆, δ): 2.3–2.6 (2H, m), 2.7–3.0 (2H, m), 3.1 (4H, br s), 3.8 (4H, br s), 6.7–6.9 (3H, s), 7.13 (1H, dd, J=2 Hz, 9 Hz), 7.40 (1H, d, J=9 Hz), 7.63 (1H, d, J=2 Hz), 9.18 (1H, s)
MASS (m/e): 442, 444, 443 (M+)

(42) 6-[4-(5-Bromoindole-2-carbonyl)-1-piperazinyl]-3,4-dihydro-2(1H)-quinolinone
mp: 273°–274° C.
IR (Nujol): 3280, 3150, 1660, 1605, 1515 cm⁻¹
NMR (DMSO-d₆, δ): 2.4–2.6 (2H, m), 2.7–3.0 (6H, m), 3.8–4.1 (4H, m), 6.87 (1H, d, J=2 Hz), 6.9–7.2 (2H, m), 7.2–7.5 (2H, m), 7.77 (1H, s), 8.76 (1H, s), 11.80 (1H, s)
MASS (m/e): 452, 454, 453 (M+)

(43) 6-[4-(5-Bromoindole-2-carbonyl)-1-piperazinyl]-2(1H)-quinolinone
mp: >280° C.
IR (Nujol): 1645, 1615, 1525, 1495 cm⁻¹
NMR (DMSO-d₆, δ): 3.0–3.4 (4H, m), 3.7–4.1 (4H, m), 6.77 (1H, d, J=10 Hz), 6.81 (1H, d, J=2 Hz), 7.1–7.5 (5H, m), 7.77 (1H, d, J=10 Hz), 7.84 (1H, s), 11.51 (1H, s), 11.78 (1H, s)
MASS (m/e): 450, 452, 451 (M+)

(44) 6-[4-(8-Methylimidazo[1,2-a]pyridine-2-carbonyl)-1-piperazinyl]-8-chloro-3,4-dihydro-2(1H)-quinolinone
mp: 240°–242° C.
IR (Nujol): 3200, 1685, 1620, 1580, 1540, 1490 cm⁻¹
NMR (D₂O+DCl, δ): 2.6–2.8 (2H, m), 2.71 (3H, s), 3.0–3.3 (2H, m), 3.9–4.2 (4H, m), 4.3–4.6 (4H, m), 7.46 (1H, d, J=7 Hz), 7.60 (1H, d, J=2 Hz), 7.73 (1H, d, J=2 Hz), 7.8–8.0 (1H, m), 8.68 (1H, d, J=7 Hz), 8.70 (1H, s)
MASS (m/e): 423 (M+)

(45) 6-[4-(5-Methylimidazo[1,2-a]pyridine-2-carbonyl)-1-piperazinyl]-3,4-dihydro-8-methyl-2(1H)-quinolinone
mp: 235°–237° C.
IR (Nujol): 3180, 3120, 1660, 1610, 1545 cm⁻¹
NMR (DMSO-d₆, δ): 2.17 (3H, s), 2.2–2.6 (2H, m), 2.62 (3H, s), 2.6–3.0 (2H, m), 2.9–3.2 (4H, m), 3.5–4.4 (4H, m), 6.63 (2H, s), 6.82 (1H, d, J=7 Hz), 7.26 (1H, dd, J=7 Hz, 9 Hz), 7.51 (1H, d, J=9 Hz), 8.17 (1H, s), 9.17 (1H, s)
MASS (m/e): 389 (M+)

(46) 6-[4-(1,2,3,4-Tetrahydro-2-oxoquinoline-6-carbonyl)-1-piperazinyl]-2(1H)-quinolinone
mp: >285° C.
IR (Nujol): 3170, 1660, 1615, 1500 cm⁻¹
NMR (DMSO-d₆, δ): 2.3–2.6 (2H, m), 2.7–3.1 (2H, m), 3.0–3.3 (4H, m), 3.5–3.8 (4H, m), 6.40 (1H, d, J=10 Hz), 6.88 (1H, d, J=9 Hz), 7.0–7.4 (5H, m), 7.76 (1H, d, J=10 Hz), 10.22 (1H, s), 11.56 (1H, s)
MASS (m/e): 402 (M+)

(47) 6-[4-(2,3-Dihydro-3,3-dimethyl-2-oxoindole-5-carbonyl)-1-piperazinyl]-3,4-dihydro-2(1H)-quinolinone
mp: >280° C.
IR (Nujol): 3200, 1725, 1675, 1665, 1605 cm⁻¹
NMR (DMSO-d₆, δ): 1.26 (6H, s), 2.7–3.1 (6H, m), 3.6–3.9 (6H, m), 6.8–7.5 (6H, m), 8.63 (1H, s), 10.47 (1H, s)
MASS (m/e): 418 (M+)

(48) 6-[4-(2,3-Dihydro-2-oxoindole-5-carbonyl)-1-piperazinyl]-3,4-dihydro-2(1H)-quinolinone
mp: 199°–200° C. (dec.)
IR (Nujol): 3140, 1720, 1620 cm⁻¹
NMR (DMSO-d₆, δ): 2.6–3.9 (14H, m), 6.7–8.3 (6H, m), 11.03 (1H, s)

(49) 6-[4-(5-Chloroindole-2-carbonyl)-1-piperazinyl]-3,4-dihydro-2(1H)-quinolinone
mp: 168°–169° C.
IR (Nujol): 3310, 3250, 3200, 1650, 1615, 1530, 1510 cm⁻¹
NMR (DMSO-d₆, δ): 2.3–2.6 (2H, m), 2.7–3.0 (2H, m), 3.1 (4H, br s), 3.9 (4H, br s), 6.7–7.0 (4H, m), 7.18 (1H, dd, J=2 Hz, 9 Hz), 7.48 (1H, d, J=9 Hz), 7.68 (1H, d, J=2 Hz), 9.90 (1H, s), 11.81 (1H, s)
MASS (m/e): 408, 410 (M+)

(50) 6-[4-(5-Hydroxyindole-2-carbonyl)-1-piperazinyl]-3,4-dihydro-2(1H)-quinolinone
mp: 287°–289° C. (dec.)
IR (Nujol): 3150, 1655, 1595, 1500 cm⁻¹
NMR (DMSO-d₆, δ): 2.27–2.59 (2H, m), 2.71–2.97 (2H, m), 3.1 (4H, br s), 3.9 (4H, br s), 6.6–6.8 (5H, m), 6.87 (1H, dd, J=2 Hz, 8 Hz), 7.27 (1H, d, J=8 Hz), 9.90 (1H, s), 11.62 (1H, s)
MASS (m/e): 390 (M+)

(51) 6-[4-(5-Methoxyindole-2-carbonyl)-1-piperazinyl]-3,4-dihydro-2(1H)-quinolinone
mp: 248°–251° C.
IR (Nujol): 3280, 1645, 1595, 1530, 1500 cm⁻¹
NMR (DMSO-d₆, δ): 2.30–2.5 (2H, m), 2.7–2.9 (2H, m), 3.0–3.3 (4H, m), 3.75 (3H, s), 3.7–4.0 (4H, m), 6.7–7.0 (5H, m), 7.12 (1H, d, J=2 Hz), 7.40 (1H, d, J=9 Hz), 9.9 (1H, br s)
MASS (m/e): 404 (M+)

(52) 6-[4-(2,4-Dimethylthiazole-5-carbonyl)-1-piperazinyl]-3,4-dihydro-2(1H)-quinolinone
mp: 199°–202° C. (dec.)
IR (Nujol): 3320, 3200, 3100, 3060, 1660, 1620, 1590 cm⁻¹
NMR (DMSO-d₆, δ): 2.33 (3H, s), 2.3–2.6 (2H, m), 2.60 (3H, s), 2.6–2.9 (2H, m), 2.9–3.2 (4H, m), 3.5–3.8 (4H, m), 6.7–6.9 (3H, m), 9.93 (1H, s)
MASS (m/e): 370 (M+)

(53) 6-[4-(2-Mesylamino-4-methylthiazole-5-carbonyl)-1-piperazinyl]-3,4-dihydro-2(1H)-quinolinone
mp: 255°–257° C.
IR (Nujol): 3170, 3110, 1670, 1620, 1555, 1500 cm⁻¹

NMR (DMSO-d$_6$, δ): 2.18 (3H, s), 2.3–2.5 (2H, m), 2.7–2.9 (2H, m), 2.94 (3H, s), 3.10 (4H, br s), 3.68 (4H, br s), 6.7–6.9 (3H, m), 9.90 (1H, s)
MASS (m/e): 449 (M+)

(54) 6-[4-(2-Methylamino-4-methylthiazole-5-carbonyl)-1-piperazinyl]-3,4-dihydro-2(1H)-quinolinone
mp: 211°–213° C.
IR (Nujol): 3320, 3170, 3050, 1665, 1630, 1500 cm$^{-1}$
NMR (DMSO-d$_6$, δ): 2.15 (3H, s), 2.3–2.5 (2H, m), 2.7–3.0 (2H, m), 2.82 (3H, d, J=5 Hz), 3.1 (4H, br s), 3.6 (4H, br s), 6.7–7.0 (3H, m), 7.8 (1H, q, J=5 Hz), 9.92 (1H, s)
MASS (m/e): 385 (M+)

(55) 6-[4-(2-Methylthioimidazole-4-carbonyl)-1-piperazinyl]-3,4-dihydro-2(1H)-quinolinone
mp: 176°–177° C.
IR (Nujol): 3120, 1675, 1600, 1560, 1540, 1510 cm$^{-1}$
NMR (D$_2$O, DCl, δ): 2.5–2.8 (2H, m), 2.87 (3H, s), 2.9–3.2 (2H, m), 3.6–4.0 (4H, m), 4.1–4.4 (4H, m), 7.08 (1H, d, J=10 Hz), 7.4–7.6 (2H, m), 8.00 (1H, s)
MASS (m/e): 371 (M+)

(56) 6-[4-{8-(2-Methylbenzyloxy)imidazo[1,2-a]pyridine-2-carbonyl}-1-piperazinyl]-3,4-dihydro-2(1H)-quinolinone
mp: 204°–206° C.
IR (Nujol): 3340, 1670, 1600, 1545 cm$^{-1}$
NMR (DMSO-d$_6$, δ): 2.37 (3H, s), 2.4–2.6 (2H, m), 2.6–3.0 (6H, m), 3.7–4.5 (4H, m), 5.29 (2H, s), 6.7–7.5 (9H, m), 8.1–8.31 (1H, m), 8.70 (1H, s)
MASS (m/e): 495 (M+)

(57) 6-[4-(7-Methylimidazo[1,2-a]pyridin-2-ylacetyl)-1-piperazinyl]-3,4-dihydro-2(1H)-quinolinone
mp: 218°–219° C.
IR (Nujol): 3180, 1680, 1640, 1505 cm$^{-1}$
NMR (D$_2$O+DCl, δ): 2.57 (3H, s), 2.5–2.8 (2H, m), 2.9–3.2 (2H, m), 3.7–4.5 (8H, m), 4.40 (2H, s), 7.06 (1H, d, J=9 Hz), 7.27 (1H, dd, J=2 Hz, 7 Hz), 7.68 (1H, dd, J=2 Hz, 9 Hz), 7.5–7.7 (2H, m), 8.00 (1H, s), 8.50 (1H, d, J=7 Hz)
MASS (m/e): 403 (M+)

(58) 6-[4-(5,8-Dimethylimidazo[1,2-a]pyridine-2-carbonyl)-1-piperazinyl]-3,4-dihydro-2(1H)-quinolinone
mp: 188°–189° C. (dec.)
IR (Nujol): 1675, 1605, 1530 cm$^{-1}$
NMR (D$_2$O, DCl, δ): 2.5–3.1 (4H, m), 2.63 (3H, s), 2.85 (3H, s), 3.0–3.4 (4H, m), 3.9–4.4 (4H, m), 6.9–7.3 (3H, m), 7.32 (1H, d, J=8 Hz), 7.80 (1H, d, J=8 Hz), 8.45 (1H, s)
MASS (m/e): 403 (M+)

(59) 6-[4-(2-Imidazo[1,2-a]pyridinecarbonyl)-1-piperazinyl]-3,4-dihydro-2(1H)-quinolinone
mp: 127°–128° C.
IR (Nujol): 3550, 3300, 1665, 1595, 1510 cm$^{-1}$
NMR (DMSO-d$_6$, δ): 2.3–2.6 (2H, m), 2.7–3.0 (2H, m), 3.0–3.3 (4H, m), 3.7–4.5 (4H, m), 6.1–7.1 (4H, m), 7.2–7.4 (1H, s), 7.51 (1H, d, J=9 Hz), 8.36 (1H, s), 8.55 (1H, d, J=7 Hz), 9.85 (1H, s)
MASS (m/e): 375 (M+)

(60) 6-[4-(2-Methylimidazo[1,2-a]pyridine-3-carbonyl)-1-piperazinyl]-3,4-dihydro-2(1H)-quinolinone
mp: 197°–199° C.
IR (Nujol): 3180, 1685, 1670, 1665, 1510 cm$^{-1}$
NMR (DMSO-d$_6$, δ): 2.3–2.6 (2H, m), 2.38 (3H, s), 2.7–3.0 (2H, m), 2.9–3.2 (4H, m), 3.5–3.8 (4H, m), 6.7–7.1 (4H, m), 7.2–7.6 (2H, m), 8.46 (1H, d, J=7 Hz), 9.85 (1H, s)
MASS (m/e): 389 (M+)

(61) 6-[4-(5-Ethylimidazo[1,2-a]pyridine-2-carbonyl)-1-piperazinyl]-3,4-dihydro-2(1H)-quinolinone
mp: 167°–168° C.
IR (Nujol): 3200, 1670, 1635, 1615 cm$^{-1}$
NMR (D$_2$O+DCl, δ): 1.48 (3H, t, J=7.5 Hz), 2.5–2.7 (2H, m), 2.8–3.0 (2H, m), 3.0–3.4 (6H, m), 3.9–4.3 (4H, m), 7.0–7.3 (3H, m), 7.40 (1H, d, J=7 Hz), 7.83 (1H, d, J=9 Hz), 8.06 (1H, dd, J=7 Hz, 9 Hz), 8.51 (1H, s)
MASS (m/e): 403 (M+)

(62) 6-[4-(2-Methylaminothiazole-4-carbonyl)-1-piperazinyl]-3,4-dihydro-2(1H)-quinolinone
mp: 202°–204° C.
IR (Nujol): 3270, 3200, 1660, 1640, 1615, 1590, 1500 cm$^{-1}$
NMR (DMSO-d$_6$, δ): 2.2–2.5 (2H, m), 2.82 (3H, d, J=5 Hz), 2.6–2.9 (2H, m), 3.0 (4H, br s), 3.7 (4H, br s), 6.6–6.8 (2H, m), 7.02 (1H, s), 7.58 (1H, q, J=5 Hz), 9.32 (1H, s)
MASS (m/e): 371 (M+)

(63) 6-[4-(3-Imidazolecarbonyl)-1-piperazinyl]-3,4-dihydro-2(1H)-quinolinone
mp: 285° C. (dec.)
IR (Nujol): 3200, 1660, 1595, 1540, 1510 cm$^{-1}$
NMR (D$_2$O+DCl, δ): 2.5–2.8 (2H, m), 2.9–3.2 (2H, m), 3.8–4.2 (4H, m), 4.2–4.5 (4H, m), 7.1 (1H, d, J=8 Hz), 7.57 (1H, dd, J=2 Hz, 8 Hz), 7.60 (1H, s), 8.13 (1H, s), 9.00 (1H, s)
MASS (m/e): 325 (M+)

(64) 6-[4-(7-Methylimidazo[1,2-a]pyridine-2-carbonyl)-1-piperazinyl]-3,4-dihydro-2(1H)-quinolinone
mp: 224°–226° C. (dec.)
IR (Nujol): 1690, 1620, 1505, 1270, 1240 cm$^{-1}$
NMR (DMSO-d$_6$, δ): 2.39 (3H, s), 2.2–2.6 (2H, m), 2.7–3.0 (2H, m), 3.0–4.5 (8H, m), 6.82 (3H, s), 6.88 (1H, dd, J=2 Hz, 8 Hz), 7.41 (1H, s), 8.31 (1H, s), 8.52 (1H, d, J=8 Hz), 9.92 (1H, s)
MASS (m/e): 389 (M+)

(65) 6-[4-(7-Methoxyimidazo[1,2-a]pyridine-2-carbonyl)-1-piperazinyl]-3,4-dihydro-2(1H)-quinolinone
mp: 127°–129° C.
IR (Nujol): 1660, 1595, 1550, 1505 cm$^{-1}$
NMR (D$_2$O+DCl, δ): 2.5–2.8 (2H, m), 2.9–3.2 (2H, m), 3.8–4.1 (4H, m), 4.06 (3H, s), 4.2–4.5 (4H, m), 7.0–7.4 (3H, m), 7.5–7.7 (1H, m), 7.62 (1H, s), 8.48 (1H, s), 8.56 (1H, d, J=9 Hz)
MASS (m/e): 405 (M+)

(66) 6-[4-{2-(2-Methyl-4-thiazolyl)acetyl}-1-piperazinyl]-3,4-dihydro-2(1H)-quinolinone
mp: 168°–169° C.
IR (Nujol): 3220, 1665, 1640, 1600, 1585 cm$^{-1}$
NMR (DMSO-d$_6$, δ): 2.3–3.0 (8H, m), 2.50 (3H, s), 3.7 (4H, br s), 3.81 (2H, s), 6.8–7.0 (3H, m), 7.17 (1H, s), 8.67 (1H, s)
MASS (m/e): 370 (M+)

(67) 6-[4-(1,2,3,4-Tetrahydro-1-methyl-2-oxoquinoline-6-carbonyl)-1-piperazinyl]-3,4-dihydro-2(1H)-quinolinone
mp: 130°–140° C.
IR (Nujol): 1640, 1610 cm$^{-1}$
NMR (DMSO-d$_6$, δ): 2.2–3.2 (12H, m), 3.22 (3H, s), 3.8–3.4 (4H, m), 6.7–7.5 (6H, m), 9.92 (1H, br s)
MASS (m/e): 418 (M+)

(68) 3,4-Dihydro-6-[4-(1H-imidazo[4,5-c]pyridine-2-carbonyl)-1-piperazinyl]-2(1H)-quinolinone
mp: >250° C.
IR (Nujol): 1670, 1630, 1615, 1560, 1505 cm$^{-1}$
NMR (DMSO-d$_6$, δ): 2.43 (2H, t, J=6.8 Hz), 2.85 (2H, t, J=6.8 Hz), 3.19 (4H, br s), 3.89 (2H, br s), 4.54 (2H, br s), 6.7–7.0 (3H, m), 7.63 (1H, d, J=5.5 Hz), 8.42 (1H, d, J=5.5 Hz), 9.09 (1H, s), 9.93 (1H, s), 13.62 (1H, br s)

MASS (m/e): 375 (M+)

(69) 3,4-Dihydro-6-[4-(5-methoxybenzimidazole-2-carbonyl)-1-piperazinyl]-2(1H)-quinolinone mp: 217°-218° C. (dec.)

IR (Nujol): 3220, 1660, 1630, 1510 cm$^{-1}$

NMR (DMSO-d$_6$, δ): 2.41 (2H, t, J=6.8 Hz), 2.84 (2H, t, J=6.8 Hz), 3.16 (4H, br s), 3.81 (3H, s), 3.86 (2H, br s), 4.67 (2H, br s), 6.8-7.8 (6H, m), 9.91 (1H, s), 13.03 (1H, s)

MASS (m/e): 405 (M+)

(70) 6-[4-(7-Methyl-5,6,7,8-tetrahydroimidazo[1,2-a]pyridine-2-carbonyl)-1-piperazinyl]-2(1H)-quinolinone mp: 245°-248° C. (dec.)

IR (Nujol): 1655, 1630, 1550, 1500 cm$^{-1}$

NMR (DMSO-d$_6$, δ): 1.06 (3H, d, J=6.4 Hz), 1.5-1.8 (1H, m), 1.8-2.1 (2H, m), 2.2-2.4 (2H, m), 2.8-3.0 (2H, m), 3.12 (4H, br s), 3.6-4.4 (4H, m), 6.45 (1H, d, J=9.5 Hz), 7.1-7.4 (3H, m), 7.54 (1H, s), 7.78 (1H, d, J=9.5 Hz), 11.58 (1H, s)

MASS (m/e): 391 (M+)

(71) 6-[4-(2-Oxo-1,2,3,4-tetrahydroquinolin-6-ylacetyl)-1-piperazinyl]-2(1H)-quinolinone mp: 201°-203° C. (dec.)

IR (Nujol): 3150, 1675, 1655, 1625, 1610 cm$^{-1}$

NMR (DMSO-d$_6$, δ): 2.40 (2H, t, J=7 Hz), 2.7-2.9 (2H, m), 3.03 (4H, br s), 3.27 (2H, s), 3.5-3.9 (4H, m), 6.41 (1H, d, J=11 Hz), 6.6-7.3 (5H, m), 7.53 (1H, d, J=9 Hz), 7.8 (1H, d, J=11 Hz), 9.97 (1H, s), 11.60 (1H, s)

MASS (m/e): 416 (M+)

EXAMPLE 4

To a mixture of 6-(1-piperazinyl)-3,4-dihydro-2(1H)-quinolinone (1.28 g), 4-chloro-6,7-dimethoxyquinazoline hydrochloride (1.43 g) and N,N-dimethylformamide (50 ml) was added triethylamine (560 mg) and the mixture was stirred for 8 hours at ambient temperature. The solvent was removed under reduced pressure and to the obtained residue were added water (20 ml), tetrahydrofuran (10 ml) and ethyl acetate (10 ml). The separated organic layer was washed with brine, dried over magnesium sulfate and concentrated. The residue was subjected to a column chromatography on silica gel (80 g) and eluted with 10% solution of methanol in chloroform. The fractions containing the object compound were combined and concentrated. The obtained residue was subjected to a column chromatography on alumina (60 g) and eluted with 5% solution of methanol in chloroform. The fractions containing the object compound were combined and concentrated to give 6-[4-(6,7-dimethoxyquinazolin-4-yl)-1-piperazinyl]-3,4-dihydro-2(1H)-quinolinone (0.8 g).

mp: 261°-262° C.

IR (Nujol): 3200, 1665, 1620, 1575, 1550, 1505 cm$^{-1}$

NMR (DMSO-d$_6$, δ): 2.2-2.5 (2H, m), 2.6-2.9 (2H, m), 3.1-3.4 (4H, m), 3.5-3.9 (4H, m), 3.95 (6H, s), 6.7-7.0 (3H, m), 7.21 (1H, s), 7.27 (1H, s), 8.62 (1H, s), 9.94 (1H, s)

MASS (m/e): 491 (M+)

EXAMPLE 5

1-Chloro-6,7-dimethoxyisoquinoline (0.63 g) and 6-(1-piperazinyl)-3,4-dihydro-2(1H)-quinolinone (1.30 g) were mixed at 200° C. for 1.5 hours under stirring. The mixture was dissolved in a mixture of chloroform and methanol (10:1 V/V) and subjected to a column chromatography on silica gel (eluent:methanol in chloroform, 0-2% V/V). The fractions containing the object compound were combined and concentrated and the residue was triturated with diisopropyl ether to give 6-[4-(6,7-dimethoxyisoquinolin-1-yl)-1-piperazinyl]-3,4-dihydro-2(1H)-quinolinone (0.44 g).

mp: 235°-240° C.

IR (Nujol): 1670, 1620 cm$^{-1}$

NMR (DMSO-d$_6$, δ): 2.2-3.7 (12H, m), 3.96 (6H, s), 6.7-7.1 (3H, m), 7.2-7.6 (3H, m), 8.05 (1H, d, J=7 Hz), 9.88 (1H, br s)

MASS (m/e): 418 (M+)

EXAMPLE 6

A mixture of 6,7-dimethoxy-1-thioxo-1,2,3,4-tetrahydroisoquinoline (1.0 g), methyl iodide (1.4 ml) and tetrahydrofuran (20 ml) was refluxed for 1 hour. Insoluble material was collected and thereto were added 6-(1-piperazinyl)-3,4-dihydro-2(1H)-quinolinone (1.04 g), triethylamine (1.25 ml) and N,N-dimethylformamide (10 ml). The mixture was stirred for 6 hours at 80° C. and poured into water (100 ml). The resulting precipitate was collected by filtration, washed with water and dried to give 6-[4-(6,7-dimethoxy-3,4-dihydroisoquinolin-1-yl)-1-piperazinyl]-3,4-dihydro-2(1H)-quinolinone (0.47 g).

mp: 70°-75° C.

IR (Nujol): 1660, 1600 cm$^{-1}$

NMR (DMSO-d$_6$, δ): 2.5-3.5 (16H, m), 3.77 (3H, s), 3.81 (3H, s), 6.6-7.0 (5H, m), 9.80 (1H, br s)

MASS (m/e): 420 (M+)

EXAMPLE 7

6-[4-(2-tert-Butoxycarbonylamino-4-methylthiazole-5-carbonyl)-1-piperazinyl]-3,4-dihydro-2(1H)-quinolinone (1.2 g) was dissolved in formic acid (25 ml) and the solution was stirred for 4 hours at ambient temperature. After the solvent was removed, ethyl acetate (10 ml) and water (10 ml) was added to the residue and the mixture was adjusted to pH 4.5 with 10% aqueous solution of potassium carbonate. The resulting precipitate was collected and recrystallized from methanol-water to give 6-[4-(2-amino-4-methylthiazole-5-carbonyl)-1-piperazinyl]-3,4-dihydro-2(1H)-quinolinone (0.9 g).

mp: 316°-318° C. (dec.)

IR (Nujol): 3300, 3200, 3100, 1670, 1620, 1510 cm$^{-1}$

NMR (DMSO-d$_6$, δ): 2.13 (3H, s), 2.2-2.4 (2H, m), 2.7-2.9 (2H, m), 2.9-3.2 (4H, m), 3.5-3.8 (4H, m), 6.7-6.8 (3H, m), 7.20 (2H, s), 9.79 (1H, s)

MASS (m/e): 371 (M+)

EXAMPLE 8

A mixture of ethyl 3-[3-[4-(7-methylimidazo[1,2-a]pyridine-2-carbonyl)-1-piperazinyl]-6-nitrophenyl]acrylate (926 mg), 10% palladium carbon (139 mg), dichloromethane (50 ml) and methanol (50 ml) was hydrogenated under one atmospheric pressure of hydrogen at ambient temperature for 2.5 hours. After filtration, acetic acid (1 ml) was added to the filtrate containing ethyl 3-[3-[4-(7-methylimidazo[1,2-a]pyridine-2-carbonyl-1-piperazinyl]-6-aminophenyl]propionate and 6-[4-(7-methylimidazo[1,2-a]-pyridine-2-carbonyl)-1-piperazinyl]-3,4-dihydro-2(1H)-quinolinone and evaporated in vacuo. The residue was dissolved in chloroform (30 ml) and washed with saturated aqueous solution of sodium hydrogene carbonate. The extract was dried over magnesium sulfate and concentrated. The residue was crystallized from ethanol to give 6-[4-(7-methylimidazo[1,2-a]-pyridine-2-carbonyl)-1-piperazinyl]-3,4-dihydro-2(1H)-quinolinone (612 mg).

mp: 224°-226° C. (dec.)

IR (Nujol): 1690, 1620, 1505, 1270, 1240 cm$^{-1}$

NMR (DMSO-d$_6$, δ): 2.39 (3H, s), 2.2–2.6 (2H,m), 2.7–3.0 (2H, m), 3.0–4.5 (8H, m), 6.82 (3H, s), 6.88 (1H, dd, J=2 Hz, 8 Hz), 7.41 (1H, s), 8.31 (1H, s), 8.52 (1H, d, J=8 Hz), 9.92 (1H, s)

MASS (m/e): 389 (M+)

EXAMPLE 9

A mixture of 7-methylimidazo[1,2-a]pyridine-2-acetic acid (571 mg), 1,1'-carbonyldiimidazole (535 mg), N,N-dimethylformamide (4.5 ml) and chloroform (7.5 ml) was stirred for 1 hour at ambient temperature. A solution of 6-(1-piperazinyl)-2(1H)-quinolinone (933 mg), triethylamine (607 mg) and dimethylsulfoxide (20 ml) was added thereto and the mixture was stirred for 2 hours at the same temperature. The resulting precipitates were collected, washed with chloroform, and dissolved in 15% solution of methanol in chloroform (30 ml) and 5% hydrochloric acid (5 ml). The mixture was adjusted to pH 9 with a saturated aqueous solution of potassium carbonate. The separated organic layer was dried over magnesium sulfate and concentrated. The residue was subjected to a column chromatography on silica gel (60 g) and eluted with 10% solution of methanol in chloroform. The fractions containing the object compound were combined and concentrated. The residue was pulverized with diethyl ether and dried to give 6-[4-(7-methylimidazo[1,2-a]pyridin-2-ylacetyl)-1-piperazinyl]-2(1H)-quinolinone (0.45 g).

mp: >250° C.

IR (Nujol): 1675, 1645, 1630, 1540, 1495 cm$^{-1}$

NMR (DMSO-d$_6$, 67 ): 2.50 (3H, s), 3.07 (4H, br s), 3.6–3.8 (4H, m), 3.62 (2H, s), 6.44 (H, d, J=9.6 Hz), 6.69 (1H, d, J=6.8 Hz), 7.0–7.3 (4H, s), 7.69 (1H, s), 7.79 (1H, d, J=9.6 Hz), 8.35 (1H, d, J=6.8 Hz), 11.55 (1H, s)

MASS (m/e): 401 (M+)

EXAMPLE 10

The following compound was obtained according to a similar manner to that of Example 9.

3,4-Dihydro-6-[4-(2-benzimidazolylacetyl)-1-piperazinyl]-2(1H)-quinolinone mp: 240°–250° C. (dec.)

IR (Nujol): 3180, 1680, 1660, 1630, 1510 cm$^{-1}$

NMR (DMSO-d$_6$, δ): 2.37 (2H, t, J=6.8 Hz), 2.50 (2H, t, J=6.8 Hz), 2.8–3.2 (4H, m), 3.4–3.8 (4H, m), 4.06 (2H, s), 6.7–6.9 (3H, m), 7.0–7.2 (2H, m), 7.4–7.6 (2H, m), 9.88 (1H, s), 12.30 (1H, s)

MASS (m/e): 389 (M+)

EXAMPLE 11

A mixture of 6-chloroacetyl-3,4-dihydro-2(1H)-quinolinone (3.3 g), 6-(1-piperazinyl)-2(1H)-quinolinone (3.11 g), triethylamine (7.5 ml), methanol (50 ml) and chloroform (50 ml) was stirred for 5 hours at 60° C. and allowed to stand overnight at ambient temperature. The resulting precipitates were collected, washed with methanol, and dried to give 6-[4-[2-(2-oxo-1,2,3,4-tetrahydroquinolin-6-yl)carbonylmethyl]-1-piperazinyl]-2(1H)-quinolinone (2.7 g).

mp: >260° C.

IR (Nujol): 1675, 1665, 1605, 1570 cm$^{-1}$

NMR (DMSO-d$_6$, +DCl, δ): 2.4–2.6(2H, m), 3.00 (2H, t, J=7.9 Hz), 3.2–3.9 (8H, m), 5.16 (2H, s), 6.61 (1H, d, J=9.5 Hz), 7.06 (1H, d, J=9.5 Hz), 7.3–7.5 (3H, m), 7.8–8.0 (3H, m)

MASS (m/e): 416 (M+)

EXAMPLE 12

The following compound was obtained according to a similar manner to that of Example 11.

6-[4-[3-(2-Oxo-1,2,3,4-tetrahydroquinolin-6-yl)-3-oxopropyl]-1-piperazinyl]-2(1H)-quinolinone mp: 253°–255° C. (dec.)

IR (Nujol): 1665, 1650, 1620, 1590 cm$^{-1}$

NMR (DMSO-d$_6$, δ): 2.4–3.5 (16H, m), 6.64 (1H, d, J=9.5 Hz), 6.94 (1H, d, J=8.1 Hz), 7.1–7.4 (3H, m), 7.7–7.9 (3H, m), 10.43 (1H, s), 11.54 (1H, s)

MASS (m/e): 430 (M+)

EXAMPLE 13

To a mixture of 6-[4-[2-(2-oxo-1,2,3,4-tetrahydroquinolin-6-yl)carbonylmethyl]-1-piperazinyl]-2(1H)-quinolinone (1.4 g), methanol (60 ml) and chloroform (160 ml) was added sodium borohydride (280 mg) over the period of 2 hours under refluxing. The mixture was stirred for 5 hours at the same temperature. After the reaction mixture was concentrated, 5% hydrochloric acid (30 ml) was added. The mixture was adjusted to pH 9 with 20% ammonium hydroxide and washed with 15% solution of methanol in chloroform (20 ml×3). Separated aqueous layer was concentrated to a volume of 10 ml and was allowed to stand overnight at ambient temperature. The resulting precipitates were collected, washed with water, and dried to give 6-[4-[2-(2-oxo-1,2,3,4-tetrahydroquinolin-6-yl)-2-hydroxyethyl]-1-piperazinyl]2(1H)-quinolinone (0.87 g).

mp: 241°–245° C. (dec.) IR (Nujol): 3250, 1660, 1640, 1605 cm$^{-1}$

NMR (DMSO-d$_6$, δ): 2.47 (2H, t, J=7 Hz), 2.88 (2H, t, J=7 Hz), 3.1–4.1 (10H, m), 5.18 (1H, br s), 6.17 (1H, br s), 6.48 (1H, d, J=11 Hz), 6.87 (1H, d, J=8 Hz), 7.1–7.5 (5H, m), 7.83 (1H, d, J=1 Hz), 10.17 (1H, s), 11.64 (1H, s)

MASS (m/e): 416 (M+)

EXAMPLE 14

The following compound was obtained according to a similar manner to that of Example 13.

6-[4-[3-(2-Oxo-1,2,3,4-tetrahydroquinolin-6-yl)-3-hydroxypropyl]-1-piperazinyl]-2(1H)-quinolinone mp: 196°–199° C. (dec.)

IR (Nujol): 1650, 1620, 1500 cm$^{-1}$

NMR (DMSO-d$_6$, δ): 1.6–1.9(2H, m), 2.2–2.6 (6H, m), 2.87 (2H, t, J=7.1 Hz), 3.0–3.4 (5H, m), 4.57 (2H, t, J=6.6 Hz), 5.4 (1H, br s), 6.45 (1H, d, J=9.5 Hz), 6.80 (1H, d, J=8 Hz), 7.0–7.3 (5H, m), 7.80 (1H, d, J=9.5 Hz), 10.05 (1H, s), 11.57 (1H, s)

MASS (m/e): 432 (M+)

EXAMPLE 15

A solution of 6-[4-(7-methylimidazo[1,2-a]pyridine-2-carbonyl)-1-piperazinyl]-3,4-dihydro-2(1H)-quinolinone (1.17 g), methanol (10 ml) and 1N-hydrochloric acid (3 ml) was concentrated under reduced pressure to a volume of 3 ml. Methanol (5 ml) was added to the solution at 60° C. The solution was allowed to stand overnight at ambient temperature to give crystals, which were collected by filtration and dried to give 6-[4-(7-methylimidazo[1,2-a]pyridine-2-carbonyl)-1-piperazinyl]-3,4-dihydro-2(1H)-quinolinone monohydrochloride (0.96 g).

mp: 274°–276° C. (dec.)

IR (Nujol): 1650, 1615, 1550, 1500 cm$^{-1}$

NMR (DMSO-d$_6$, δ): 2.43 (2H, t, J=6.9 Hz), 2.50 (3H, s), 2.86 (2H, t, J=6.9 Hz), 3.32 (4H, s), 3.7–4.3 (4H, m), 6.85 (1H, d, J=8.4 Hz), 6.9–7.2 (2H, m), 7.25 (1H, d, J=7.0 Hz), 7.65 (1H, s), 8.71 (1H, s), 8.73 (H, d, J=8.4 Hz), 10.06 (1H, s)

EXAMPLE 16

A solution of 6-[4-(7-methylimidazo[1,2-a]pyridine-2-carbonyl)-1-piperazinyl]-3,4-dihydro-2(1H)-quinolinone (10.1 g), methanol (100 ml) and 1N-hydrochloric acid (52 ml) was concentrated under reduced pressure to a volume of 30 ml. Methanol (50 ml) was added to the solution at 60° C. The solution was allowed to stand overnight at ambient temperature to give crystals, which were collected by filtration and dried to give 6-[4-(7-methylimidazo[1,2-a]pyridine-2-carbonyl)-1-piperazinyl]-3,4-dihydro-2(1H)-quinolinone dihydrochloride (5.7 g).

mp: 234°–237° C. (dec.)

IR (Nujol): 1700, 1655, 1640 cm$^{-1}$

NMR (DMSO-d$_6$, δ): 2.47 (2H, t, J=7.9 Hz), 2.55 (3H, s), 2.91 (2H, t, J=7.9 Hz), 3.65 (4H, br s), 4.22 (4H, br s), 6.99 (1H, d, J=8.6 Hz), 7.41 (1H, dd, J=12 Hz, 7.0 Hz), 7.61 (1H, d, J=8.6 Hz), 7.68 (1H, s), 7.77 (1H, s), 8.85 (1H, d, J=7 Hz), 8.92 (1H, s), 10.33 (1H, s)

EXAMPLE 17

The following compound was obtained according to a similar manner to that of Example 15.

6-[4-(7-Methylimidazo[1,2-a]pyridine-2-carbonyl)-1-piperazinyl]-3,4-dihydro-2(1H)-quinolinone methanesulfonate mp: 226°–229° C.

IR (Nujol): 2400, 1635, 1510 cm$^{-1}$

NMR (DMSO-d$_6$, δ): 2.41 (3H, s), 2.42 (2H, t, J=7.0 Hz), 2.53 (3H, s), 2.85 (2H, t, J=7.0 Hz), 3.24 (4H, s), 3.96 (4H, br s), 6.7–7.0 (3H, m), 7.33 (H, d, J=7.0 Hz), 7.68 (1H, s), 8.73 (1H, s), 8.75 (1H, d, J=7.9 Hz), 9.97 (1H, s)

EXAMPLE 18

A solution of 6-[4-(7-methylimidazo[1,2-a]pyridine-2-carbonyl)-1-piperazinyl]-3,4-dihydro-2(1H)-quinolinone (195 mg) and maleic acid (58 mg) in ethanol (30 ml) was concentrated under reduced pressure to a volume of 3 ml. The solution under heating at 60° C. was diluted with ethyl acetate (10 ml) and allowed to stand overnight at ambient temperature to give crystals, which were collected by filtration to give 6-[4-(7-methylimidazo[1,2-a]pyridine-2-carbonyl)-1-piperazinyl]-3,4-dihydro-2(1H)-quinolinone hemimaleate (0.23 g).

mp: 235°–237° C.

IR (Nujol): 1660, 1610, 1580 cm$^{-1}$

NMR (DMSO-d$_6$, δ): 2.39 (3H, s), 2.41 (2H, t, J=7.9 Hz), 2.83 (2H, t, J=7.9 Hz), 3.11 (4H, br s), 3.80 (2H, br s), 4.31 (2H, br s), 6.24 (1H, s), 6.7–7.0 (4H, m), 7.43 (1H, s), 8.33 (1H, s), 8.49 (1H, d, J=6.9 Hz), 9.89 (1H, s)

EXAMPLE 19

The following compounds were obtained according to a similar manner to that of Example 8.

(1) 6-[4-(5-Methylimidazo[1,2-a]pyridine-2-carbonyl)-1-3,4-dihydro-2(1H)-quinolinone mp: 238°–240° C. (dec.)

IR (Nujol): 3440, 1650, 1610, 1540 cm$^{-1}$ (2) 6-[4-(5-Methylimidazo[1,2-a]pyridine-2-carbonyl)-1-piperazinyl]-8-chloro-3,4-dihydro-2(1H)-quinolinone mp: 230°–232° C.

IR (Nujol): 1668, 1605, 1580, 1540 cm$^{-1}$ (3) 6-[4-(1-Methylindole-2-carbonyl)-1-piperazinyl]-3,4-dihydro-2(1H)-quinolinone mp: 142°–144° C.

IR (Nujol): 1660, 1600, 1510 cm$^{-1}$ (4) 6-[4-(7-Methylimidazo[1,2-a]pyridine-2-carbonyl)-1-piperazinyl]-8-chloro-3,4-dihydro-2(1H)-quinolinone mp: 199°–200° C.

IR (Nujol): 1675, 1630, 1600, 1575 cm$^{-1}$ (5) 6-[4-(3-Indolecarbonyl)-1-piperazinyl]-3,4-dihydro-2(1H)-quinolinone mp: 268°–269° C. (dec.)

IR (Nujol): 3410, 3210, 1660, 1600, 1530, 1500 cm$^{-1}$ (6) 6-[4-(2-Indolecarbonyl)-1-piperazinyl]-3,4-dihydro-2(1H)-quinolinone mp: 233°–235° C.

IR (Nujol): 3250, 1665, 1595, 1520, 1500 cm$^{-1}$ (7) 6-[4-(5-Methylindole-2-carbonyl)-1-piperazinyl]-3,4-dihydro-2(1H)-quinolinone mp: 165°–167° C.

IR (Nujol): 3280, 3040, 1650, 1610 cm$^{-1}$ (8) 6-[4-(2-Methylthiazole-4-carbonyl)-1-piperazinyl]-3,4-dihydro-2(1H)-quinolinone mp: 155°–156° C.

IR (Nujol): 3180, 1675, 1605, 1500 cm$^{-1}$ (9) 6-[4-(2-Amino-4-ethylthiazole-5-carbonyl)-1-piperazinyl]-3,4-dihydro-2(1H)-quinolinone mp: 204°–206° C.

IR (Nujol): 3330, 3270, 3100, 1650, 1605, 1590 cm$^{-1}$

(10) 6-[4-(2-Benzimidazolecarbonyl)-1-piperazinyl]-3,4-dihydro-2(1H)-quinolinone mp: 291°–294° C. (dec.)

IR (Nujol): 3240, 1670, 1610, 1510 cm$^{-1}$

(11) 6-[4-(2-tert-Butoxycarbonylamino-4-methylthiazole-5-carbonyl)-1-piperazinyl]-3,4-dihydro-2(1H)-quinolinone mp: 162°–163° C.

IR (Nujol): 3200, 1705, 1655, 1620, 1550, 1505 cm$^{-1}$

(12) 6-[4-(2-Methylamino-4-ethylthiazole-5-carbonyl)-1-piperazinyl]-3,4-dihydro-2(1H)-quinolinone mp: 218°–220° C. (dec.)

IR (Nujol): 3330, 3200, 3110, 1665, 1600, 1505 cm$^{-1}$

(13) 6-[4-(5-Bromoindole-2-carbonyl)-1-piperazinyl]-8-methyl-3,4-dihydro-2(1H)-quinolinone mp: 255°–260° C.

IR (Nujol): 1665, 1615, 1595 cm$^{-1}$

(14) 6-[4-(5-Chloroindole-2-carbonyl)-1-piperazinyl]-8-methyl-3,4-dihydro-2(1H)-quinolinone mp: 257°–259° C.

IR (Nujol): 1665, 1620, 1530 cm$^{-1}$

(15) 6-[4-(7-Methylimidazo[1,2-a]pyridine-2-carbonyl)-1-piperazinyl]-8-methyl-3,4-dihydro-2(1H)-quinolinone mp: 233°–234° C.

IR (Nujol): 1670, 1605, 1550, 1500 cm$^{-1}$

(16) 6-[4-(1,2,3,4-Tetrahydro-2-oxoquinoline-6-carbonyl)1-piperazinyl]-8-methyl-3,4-dihydro-2(1H)-quinolinone mp: >260° C.

IR (Nujol): 1675, 1630, 1610, 1490 cm$^{-1}$

(17) 6-[4-(1,2,3,4-Tetrahydro-2-oxoquinoline-6-carbonyl)1-piperazinyl]-3,4-dihydro-2(1H)-quinolinone mp: 160°–170° C.

IR (Nujol): 1650, 1600 cm$^{-1}$

(18) 6-[4-(7-Ethylimidazo[1,2-a]pyridine-2-carbonyl)-1-piperazinyl]-3,4-dihydro-2(1H)-quinolinone mp: 200°–201° C.
IR (Nujol): 1670, 1605, 1550, 1505 cm$^{-1}$

(19) 6-[4-(7,8-Dimethylimidazo[1,2-a]pyridine-2-carbonyl)-1-piperazinyl]-3,4-dihydro-2(1H)-quinolinone
mp: 234°–235° C.
IR (Nujol): 3210, 1670, 1625, 1550, 1510 cm$^{-1}$

(20) 6-[4-(7-Isopropylimidazo[1,2-a]pyridine-2-carbonyl)-1-piperazinyl]-3,4-dihydro-2(1H)-quinolinone
mp: 200°–201° C.
IR (Nujol): 3180, 3150, 1655, 1600, 1540, 1510 cm$^{-1}$

(21) 6-[4-(8-Ethylimidazo[1,2-a]pyridine-2-carbonyl)-1-piperazinyl]-3,4-dihydro-2(1H)-quinolinone
mp: 218°–220° C.
IR (Nujol): 3200, 1670, 1620, 1540, 1500 cm$^{-1}$

(22) 6-[4-(8-Acetamidoimidazo[1,2-a]pyridine-2-carbonyl)-1-piperazinyl]-3,4-dihydro-2(1H)-quinolinone
mp: 303°–306° C. (dec.)
IR (Nujol): 3180, 1670, 1660, 1655, 1615, 1545, 1510 cm$^{-1}$

(23) 6-[4-(2-Methylimidazo[1,2-a]pyridine-6-carbonyl)-1-piperazinyl]-3,4-dihydro-2(1H)-quinolinone
mp: 257°–259° C.
IR (Nujol): 1670, 1640, 1605, 1510 cm$^{-1}$

(24) 6-[4-{2-Methylamino-5-(4-pyridyl)thiazole-4-carbonyl}-1-piperazinyl]-3,4-dihydro-2(1H)-quinolinone
mp: 290°–294° C. (dec.)
IR (Nujol): 3200, 1670, 1640, 1610, 1590, 1510 cm$^{-1}$

(25) 6-[4-(2,5-Dimethylthiazole-4-carbonyl)-1-piperazinyl]-3,4-dihydro-2(1H)-quinolinone
mp: 179°–180° C.
IR (Nujol): 3250, 1665, 1625, 1485 cm$^{-1}$

(26) 6-[4-(5-Indolecarbonyl)-1-piperazinyl]-3,4-dihydro-2(1H)-quinolinone
mp: 268° C. (dec.)
IR (Nujol): 3150, 1650, 1600, 1500 cm$^{-1}$

(27) 6-[4-(6-Chloroimidazo[1,2-a]pyridine-2-carbonyl)-1-piperazinyl]-3,4-dihydro-2(1H)-quinolinone
mp: 300°–303° C. (dec.)
IR (Nujol): 3150, 1680, 1625, 1535, 1510 cm$^{-1}$

(28) 6-[4-(3,7-Dimethylimidazo[1,2-a]pyridine-2-carbonyl)-1-piperazinyl]-3,4-dihydro-2(1H)-quinolinone
mp: 206°–208° C.
IR (Nujol): 3180, 1655, 1620, 1555, 1505 cm$^{-1}$

(29) 6-[4-(7-Chloroimidazo[1,2-a]pyridine-2-carbonyl)-1-piperazinyl]-3,4-dihydro-2(1H)-quinolinone
mp: 238°–241° C. (dec.)
IR (Nujol): 3380, 3230, 1665, 1630, 1590, 1545, 1505 cm$^{-1}$

(30) 6-[4-(7-Cyanoimidazo[1,2-a]pyridine-2-carbonyl)-1-piperazinyl]-3,4-dihydro-2(1H)-quinolinone
mp: 305°–307° C. (dec.)
IR (Nujol): 3180, 3080, 2225, 1670, 1605, 1505 cm$^{-1}$

(31) 6-[4-(6-Methylimidazo[1,2-a]pyridine-2-carbonyl)-1-piperazinyl]-3,4-dihydro-2(1H)-quinolinone
mp: 289°–290° C. (dec.)
IR (Nujol): 3140, 1665, 1595, 1560, 1505 cm$^{-1}$

(32) 6-[4-(8-Methylimidazo[1,2-a]pyridine-2-carbonyl)-1-piperazinyl]-3,4-dihydro-2(1H)-quinolinone
mp: 272°–274° C.
IR (Nujol): 3190, 3060, 1670, 1620, 1545 cm$^{-1}$

(33) 6-[4-(5,7-Dimethylimidazo[1,2-a]pyridine-2-carbonyl)-1-piperazinyl]-3,4-dihydro-2(1H)-quinolinone
mp: 243°–244° C.
IR (Nujol): 3430, 1675, 1645, 1615, 1555 cm$^{-1}$

(34) 6-[4-(3-Methyl-6-nitroimidazo[1,5-a]pyridine-1-carbonyl)-1-piperazinyl]-3,4-dihydro-2(1H)quinolinone
mp: 256°–258° C.
IR (Nujol): 3400, 1685, 1670, 1640, 1590, 1540 1505 cm$^{-1}$

(35) 6-[4-(5-Chloroindole-2-carbonyl)-1-piperazinyl]-3,4-dihydro-8-chloro-2(1H)-quinolinone
mp: 249°–250° C.
IR (Nujol): 3180, 1680, 1660, 1625, 1575, 1535 cm$^{-1}$

(36) 6-[4-(5-Bromoindole-2-carbonyl)-1-piperazinyl]-3,4-dihydro-2(1H)-quinolinone
mp: 273°–274° C.
IR (Nujol): 3280, 3150, 1660, 1605, 1515 cm$^{-1}$

(37) 6-[4-(8-Methylimidazo[1,2-a]pyridine-2-carbonyl)-1-piperazinyl]-8-chloro-3,4-dihydro-2(1H)-quinolinone
mp: 240°–242° C.
IR (Nujol): 3200, 1685, 1620, 1580, 1540, 1490 cm$^{-1}$

(38) 6-[4-(5-Methylimidazo[1,2-a]pyridine-2-carbonyl)-1-piperazinyl]-3,4-dihydro-8-methyl-2(1H)-quinolinone
mp: 235°–237° C.
IR (Nujol): 3180, 3120, 1660, 1610, 1545 cm$^{-1}$

(39) 6-[4-(2,3-Dihydro-3,3-dimethyl-2-oxoindole-5-carbonyl)-1-piperazinyl]-3,4-dihydro-2(1H)quinolinone
mp: >280° C.
IR (Nujol): 3200, 1725, 1675, 1665, 1605 cm$^{-1}$

(40) 6-[4-(2,3-Dihydro-2-oxoindole-5-carbonyl)-1-piperazinyl]-3,4-dihydro-2(1H)-quinolinone
mp: 199°–200° C. (dec.)
IR (Nujol): 3140, 1720, 1620 cm$^{-1}$

(41) 6-[4-(5-Chloroindole-2-carbonyl)-1-piperazinyl]-3,4-dihydro-2(1H)-quinolinone
mp: 168°–169° C.
IR (Nujol): 3310, 3250, 3200, 1650, 1615, 1530, 1510 cm$^{-1}$

(42) 6-[4-(5-Hydroxyindole-2-carbonyl)-1-piperazinyl]-3,4-dihydro-2(1H)-quinolinone
mp: 287°–289° C. (dec.)
IR (Nujol): 3150, 1655, 1595, 1500 cm$^{-1}$

(43) 6-[4-(5-Methoxyindole-2-carbonyl)-1-piperazinyl]-3,4-dihydro-2(1H)-quinolinone
mp: 248°–251° C.
IR (Nujol): 3280, 1645, 1595, 1530, 1500 cm$^{-1}$

(44) 6-[4-(2,4-Dimethylthiazole-5-carbonyl)-1-piperazinyl]-3,4-dihydro-2(1H)-quinolinone
mp: 199°–202° C. (dec.)
IR (Nujol): 3320, 3200, 3100, 3060, 1660, 1620, 1590 cm$^{-1}$

(45) 6-[4-(2-Mesylamino-4-methylthiazole-5-carbonyl)-1-piperazinyl]-3,4-dihydro-2(1H)-quinolinone
mp: 255°–257° C.
IR (Nujol): 3170, 3110, 1670, 1620, 1555, 1500 cm$^{-1}$

(46) 6-[4-(2-Methylamino-4-methylthiazole-5-carbonyl)-1-piperazinyl]-3,4-dihydro-2(1H)-quinolinone
mp: 211°–213° C.
IR (Nujol): 3320, 3170, 3050, 1665, 1630, 1500 cm$^{-1}$

(47) 6-[4-(2-Methylthioimidazole-4-carbonyl)-1-piperazinyl]-3,4-dihydro-2(1H)-quinolinone
mp: 176°–177° C.
IR (Nujol): 3120, 1675, 1600, 1560, 1540, 1510 cm$^{-1}$

(48) 6-[4-{8-(2-Methylbenzyloxy)imidazo[1,2-a]pyridine-2-carbonyl}-1-piperazinyl]-3,4-dihydro-2(1H)-quinolinone
mp: 204°–206° C.
IR (Nujol): 3340, 1670, 1600, 1545 cm$^{-1}$

(49) 6-[4-(7-Methylimidazo[1,2-a]pyridin-2-ylacetyl)-1-piperazinyl]-3,4-dihydro-2(1H)-quinolinone
mp: 218°–219° C.
IR (Nujol): 3180, 1680, 1640, 1505 cm$^{-1}$

(50) 6-[4(5,8-Dimethylimidazo[1,2-a]pyridine-2-carbonyl)-1-piperazinyl]-3,4-dihydro-2(1H)-quinolinone
mp: 188°–189° C. (dec.)
IR (Nujol): 1675, 1605, 1530 cm$^{-1}$

(51) 6-[4-(2-Imidazo[1,2-a]pyridinecarbonyl)-1-piperazinyl]-3,4-dihydro-2(1H)-quinolinone mp: 127°–128° C.
IR (Nujol): 3550, 3300, 1665, 1595, 1510 cm⁻¹

(52) 6-[4-(2-Methylimidazo[1,2-a]pyridine-3-carbonyl)-1-piperazinyl]-3,4-dihydro-2(1H)-quinolinone
mp: 197°–199° C.
IR (Nujol): 3180, 1685, 1670, 1665, 1510 cm⁻¹

(53) 6-[4-(5-Ethylimidazo[1,2-a]pyridine-2-carbonyl)-1-piperazinyl]-3,4-dihydro-2(1H)-quinolinone
mp: 167°–168° C.
IR (Nujol): 3200, 1670, 1635, 1615 cm⁻¹

(54) 6-[4-(2-Methylaminothiazole-4-carbonyl)-1-piperazinyl]-3,4-dihydro-2(1H)-quinolinone
mp: 202°–204° C.
IR (Nujol): 3270, 3200, 1660, 1640, 1615, 1590, 1500 cm⁻¹

(55) 6-[4-(3-Imidazolecarbonyl)-1-piperazinyl]-3,4-dihydro-2(1H)-quinolinone
mp: 285° C. (dec.)
IR (Nujol): 3200, 1660, 1595, 1540, 1510 cm⁻¹

(56) 6-[4-(7-Methoxyimidazo[1,2-a]pyridine-2-carbonyl)-1-piperazinyl]-3,4-dihydro-2(1H)-quinolinone
mp: 127°–129° C.
IR (Nujol): 1660, 1595, 1550, 1505 cm⁻¹

(57) 6-[4-{2-(2-Methyl-4-thiazolyl)acetyl}-1-piperazinyl]-3,4-dihydro-2(1H)-quinolinone
mp: 168°–169° C.
IR (Nujol): 3220, 1665, 1640, 1600, 1585 cm⁻¹

(58) 6-[4-(1,2,3,4-Tetrahydro-1-methyl-2-oxoquinoline-6-carbonyl)-1-piperazinyl]-3,4-dihydro-2(1H)quinolinone
mp: 130°–140° C.
IR (Nujol): 1640, 1610 cm⁻¹

(59) 6-[4-(6,7-Dimethoxyquinazolin-4-yl)-1-piperazinyl]-3,4-dihydro-2(1H)-quinolinone
mp: 261°–262° C.
IR (Nujol): 3200, 1665, 1620, 1575, 1550, 1505 cm⁻¹

(60) 6-[4-(6,7-Dimethoxyisoquinolin-1-yl)-1-piperazinyl]-3,4-dihydro-2(1H)-quinolinone
mp: 235°–240° C.
IR (Nujol): 1670, 1620 cm⁻¹

(61) 6-[4-(6,7-Dimethoxy-3,4-dihydroisoquinolin-1-yl)-1-piperazinyl]-3,4-dihydro-2(1H)-quinolinone
mp: 70°–75° C.
IR (Nujol): 1660, 1600 cm⁻¹

(62) 6-[4-(2-Amino-4-methylthiazole-5-carbonyl)-1-piperazinyl]-3,4-dihydro-2(1H)-quinolinone
mp: 316°–318° C. (dec.)
IR (Nujol): 3300, 3200, 3100, 1670, 1620, 1510 cm⁻¹

(63) 3,4-Dihydro-6-[4-(1H-imidazo[4,5-c]pyridine-2-carbonyl)-1-piperazinyl]-2(1H)-quinolinone
mp: >250° C.
IR (Nujol): 1670, 1630, 1615, 1560, 1505 cm⁻¹

(64) 3,4-Dihydro-6-[4-(5-methoxybenzimidazole-2-carbonyl)1-piperazinyl]-2(1H)-quinolinone
mp: 217°–218° C.
IR (Nujol): 3220, 1660, 1630, 1510 cm⁻¹

(65) 3,4-Dihydro-6-[4-(2-benzimidazolylacetyl)-1-piperazinyl]-2(1H)-quinolinone
mp: 240°–250° C. (dec.)
IR (Nujol): 3180, 1680, 1660, 1630, 1510 cm⁻¹

What we claim is:

1. A compound of the formula:

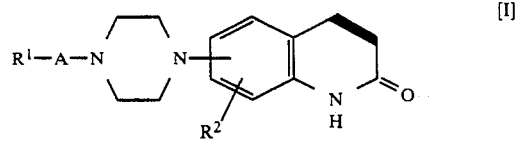

[I]

wherein
R¹ is imidazopyridyl, thiazolyl, indolyl, dihydroindolyl, imidazolyl, benzimidazolyl, quinolyl, isoquinolyl, quinazolinyl, dihydroisoquinolyl, tetrahydroimidazopyridyl or tetrahydroquinolyl, each of which may be substitute with substituent(s) selected from the group consisting of lower alkyl, halogen, lower alkoxy, lower alkylthio, ar(lower-)alkoxy, cyano, nitro, amino, lower alkylamino, acylamino, hydroxy and oxo,
R² is hydrogen, lower alkyl or halogen,
A is a single bond or a group of the formula selected from the group consisting of:

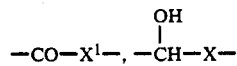

and —X—CO—, in which X is a single bond or lower alkylene and X¹ is lower alkylene, and a heavy solid line means a single or a double bond, and its pharmaceutically acceptable salt.

2. A compound of claim 1, wherein
R¹ is imidazopyridyl substituted with lower alkyl,
R² is hydrogen,
A is —CO—, and
a heavy solid line means a single bond.

3. A compound of claim 2, wherein
R¹ is imidazo[1,2-a]pyridyl substituted with methyl.

4. A compound of claim 3, which is 6-[4-(7-methylimidazo[1,2-a]pyridine-2-carbonyl)-1-piperazinyl]-3,4-dihydro-2(1H)-quinolinone, its monohydrochloride, its dihydrochloride, its methanesulfonate or its hemimaleate.

5. A pharmaceutical composition comprising a compound of claim 1, as an active ingredient, in association with a pharmaceutically acceptable, substantially nontoxic carrier or excipient.

6. A method for therapeutic treatment of heart disease or hypertension which comprises administering an effective amount of a compound of claim 1 to human beings or animals.

* * * * *